(12) United States Patent
Farb et al.

(10) Patent No.: US 11,459,399 B2
(45) Date of Patent: Oct. 4, 2022

(54) PHARMACEUTICAL COMPOSITIONS OF A HER2/NEU ANTIBODY AND USE OF THE SAME

(71) Applicant: MacroGenics, Inc., Rockville, MD (US)

(72) Inventors: David Lee Farb, Chelmsford, MA (US); Yan Zhou, Rockville, MD (US); Krishnan Sampathkumar, North Potomac, MD (US)

(73) Assignee: MacroGenics, Inc., Rockville, MD (US)

( * ) Notice: Subject to any disclaimer, the term of this patent is extended or adjusted under 35 U.S.C. 154(b) by 0 days.

(21) Appl. No.: 17/541,926

(22) Filed: Dec. 3, 2021

(65) Prior Publication Data

US 2022/0177602 A1    Jun. 9, 2022

Related U.S. Application Data

(63) Continuation of application No. PCT/US2021/061553, filed on Dec. 2, 2021.

(60) Provisional application No. 63/233,588, filed on Aug. 16, 2021, provisional application No. 63/174,766, filed on Apr. 14, 2021, provisional application No. 63/121,279, filed on Dec. 4, 2020.

(51) Int. Cl.
| | |
|---|---|
| *A61K 39/395* | (2006.01) |
| *C07K 16/32* | (2006.01) |
| *A61K 47/02* | (2006.01) |
| *A61P 35/00* | (2006.01) |
| *A61K 47/26* | (2006.01) |
| *A61K 47/18* | (2017.01) |

(52) U.S. Cl.
CPC .............. *C07K 16/32* (2013.01); *A61K 47/02* (2013.01); *A61K 47/183* (2013.01); *A61K 47/26* (2013.01); *A61P 35/00* (2018.01)

(58) Field of Classification Search
None
See application file for complete search history.

(56) References Cited

U.S. PATENT DOCUMENTS

| | | |
|---|---|---|
| 5,821,337 A | 10/1998 | Carter et al. |
| 6,399,063 B1 | 6/2002 | Hudziak et al. |
| 6,627,196 B1 | 9/2003 | Baughman et al. |
| 7,097,840 B2 | 8/2006 | Erickson et al. |
| 7,371,376 B1 | 5/2008 | Fendly |
| 7,371,379 B2 | 5/2008 | Baughman et al. |
| 7,435,797 B2 | 10/2008 | Lowman et al. |
| 7,575,748 B1 | 8/2009 | Erickson et al. |
| 7,618,631 B2 | 11/2009 | Sliwkowski |
| 7,648,702 B2 * | 1/2010 | Gombotz .................. A61P 1/16 424/134.1 |
| 7,846,441 B1 | 12/2010 | Hellmann |
| 7,850,966 B2 | 12/2010 | Lowman et al. |
| 7,862,817 B2 | 1/2011 | Adams et al. |
| 7,892,549 B2 | 2/2011 | Paton et al. |
| 8,075,892 B2 | 12/2011 | Hellmann |
| 8,309,087 B2 | 11/2012 | Hellmann |
| 8,425,908 B2 | 4/2013 | Hellmann |
| 8,591,897 B2 | 11/2013 | Bryant |
| 8,642,036 B2 | 2/2014 | Hellmann |
| 8,802,093 B2 | 8/2014 | Johnson et al. |
| 9,243,069 B2 | 1/2016 | Johnson et al. |
| 9,345,661 B2 | 5/2016 | Adler et al. |
| 9,469,692 B2 | 10/2016 | Johnson et al. |
| 9,968,676 B2 | 5/2018 | Adler et al. |
| 10,131,713 B2 | 11/2018 | Johnson et al. |
| 10,160,811 B2 | 12/2018 | Baughman et al. |
| 10,280,228 B2 | 5/2019 | Baughman et al. |
| 10,590,182 B2 | 3/2020 | Lim et al. |
| 10,675,358 B2 | 6/2020 | Alonso et al. |
| 10,689,457 B2 | 6/2020 | Paton et al. |
| 10,973,826 B2 | 4/2021 | Cortez et al. |
| 11,028,183 B2 | 6/2021 | Johnson et al. |
| 11,078,279 B2 | 8/2021 | Wigginton et al. |
| 11,110,178 B2 | 9/2021 | Alonso et al. |
| 2011/0097323 A1 | 4/2011 | Johnson et al. |

(Continued)

FOREIGN PATENT DOCUMENTS

| | | |
|---|---|---|
| WO | WO 2009/123894 | 10/2009 |
| WO | WO 2015/095418 | 6/2015 |
| WO | WO 2016/201051 | 12/2016 |

OTHER PUBLICATIONS

Bang, J.Y. et al. (2017) "*First-In-Human Phase 1 Study Of Margetuximab (MGAH22), An Fc-Modified Chimeric Monoclonal Antibody, In Patients With HER2-Positive Advanced Solid Tumors*," Annals of Oncology 28(4):855-861.

Jena Bioscience GmbH "*Screen Formulation For final 1x buffer FORMOscreen(R) Antibody Formulation Screen*," Product information sheet (online) Jul. 1, 2020 [URL:Https://www.jenabioscience.com/images/Of4b2c43de/CS-360_FORMOscreen_formulation.pdf]; pp. 1-4.

Anonymous (2020) MARGENZA® Label Prescribing Information; 17 pages.

(Continued)

*Primary Examiner* — Yunsoo Kim

(74) *Attorney, Agent, or Firm* — Jeffrey I. Auerbach; AuerbachSchrot LLC

(57) ABSTRACT

The present invention is directed in part to pharmaceutical compositions for storage and administration comprising a) a HER2/neu antibody ("margetuximab"), b) buffering agents, and c) stabilizers, wherein said margetuximab is stable. The invention in part provides, containers and kits comprising such pharmaceutical compositions. The invention is directed in part to the use of such pharmaceutical compositions, containers, and kits containing margetuximab in the treatment of HER2/neu-positive cancer (i.e., a cancer that expresses HER2), including breast cancer or gastric cancer or GEJ cancer.

13 Claims, No Drawings

Specification includes a Sequence Listing.

(56) References Cited

U.S. PATENT DOCUMENTS

| | | |
|---|---|---|
| 2014/0328836 A1 | 11/2014 | Johnson et al. |
| 2016/0051695 A1 | 2/2016 | Lin et al. |
| 2016/0130360 A1 | 5/2016 | Johnson et al. |
| 2017/0028079 A1 | 2/2017 | Li |
| 2017/0056391 A1 | 3/2017 | Li |
| 2017/0056504 A1 | 3/2017 | Kohn et al. |
| 2017/0121421 A1 | 5/2017 | Cortez et al. |
| 2017/0218083 A1 | 8/2017 | Johnson et al. |
| 2018/0036285 A1 | 2/2018 | Tunac et al. |
| 2018/0208636 A1 | 7/2018 | Lim et al. |
| 2018/0298100 A1 | 10/2018 | Wigginton et al. |
| 2018/0362624 A1 | 12/2018 | Gouilleux-Gruart et al. |
| 2019/0099415 A1 | 4/2019 | Li |
| 2019/0256611 A1 | 8/2019 | Raby et al. |
| 2019/0262466 A1 | 8/2019 | Van Berkel et al. |
| 2020/0002704 A1 | 1/2020 | Huang et al. |
| 2020/0023076 A1 | 1/2020 | Fotin-Mleczek et al. |
| 2020/0071380 A1 | 3/2020 | Schreiber et al. |
| 2020/0108151 A1 | 4/2020 | Jackson et al. |
| 2020/0188401 A1 | 6/2020 | Peterson et al. |
| 2020/0188528 A1 | 6/2020 | Olson et al. |
| 2020/0206357 A1 | 7/2020 | Olson et al. |
| 2020/0239571 A1 | 7/2020 | Bramson et al. |
| 2020/0254094 A1 | 8/2020 | Shenoy |
| 2020/0276327 A1 | 9/2020 | Li |
| 2021/0002339 A1 | 1/2021 | Real Garcia et al. |
| 2021/0145834 A1 | 5/2021 | Reddy |
| 2021/0154316 A1 | 5/2021 | Alonso et al. |
| 2021/0239702 A1 | 8/2021 | Scaltriti et al. |
| 2021/0246211 A1 | 8/2021 | Goldberg et al. |
| 2021/0261649 A1 | 8/2021 | Parry et al. |
| 2021/0363270 A1 | 11/2021 | Park et al. |

OTHER PUBLICATIONS

Anonymous, "Margetuximab Plus Chemotherapy vs Trastuzumab Plus Chemotherapy in the Treatment of HER2+ Metastatic Breast Cancer (SOPHIA)," ClinicalTrials.gov (8 pages).

Bang, Y.J. et al. (2017) "First-In-Human Phase 1 Study Of Margetuximab (MGAH22), An Fc-Modified Chimeric Monoclonal Antibody, In Patients With HER2-Positive Advanced Solid Tumors," Ann Oncol. 28(4):855-861.

Burris, H.A.. (2013) "Phase I Study Of margetuximab (MGAH22), An FC-Modified Chimeric Monoclonal Antibody (MAb), in Patients (pts) With Advanced Solid Tumors Expressing The HER2 Oncoprotein," J. Clin. Oncol. Suppl: abstr. 3004; 2 pages.

Burstein, H.J. (2005) "The Distinctive Nature of HER2-Positive Breast Cancers," N. Engl. J. Med. 353 (16): 1652-1654.

Catenacci, D.V. et al. (2020) "MAHOGANY: Margetuximab Combination In HER2+ Unresectable/Metastatic Gastric/Gastroesophageal Junction Adenocarcinoma," Future Oncol. 17(10):1155-1164.

Catenacci, D.V.T. et al. (2020) "CP-MGAH22-5 Study Group. Margetuximab plus pembrolizumab in patients with previously treated, HER2-positive gastro-oesophageal adenocarcinoma (CP-MGAH22-05): a single-arm, phase 1b-2 trial," Lancet Oncol. 21(8):1066-1076.

Cobleigh, M.A. et al. (1999) "Multinational Study Of The Efficacy And Safety Of Humanized anti-HER2 Monoclonal Antibody In Women Who Have HER2-Overexpressing Metastatic Breast Cancer That Has Progressed After Chemotherapy For Metastatic Disease," J. Clin. Oncol. 17:2639-2648.

Henriques, B. et al. (2021). Immunotherapy in Breast Cancer: When, How, and What Challenges? Biomedicines 9(11):1687:1-22.

Karrels, J. et al. (2015) "MacroGenics Presents Updated Data from Phase 1 Study of Margetuximab at ASCO Annual Meeting 2015," Retrieved from the Internet: URL:http://ir.macrogenics.com/static-files/dc17198f-ce6e-4de0-a58ae55f439487642; pages.

Kreutzfeldt, J. et al. (2020) "The Trastuzumab Era: Current And Upcoming Targeted HER2+ Breast Cancer Therapies," Am. J. Cancer Res. 10(4):1045-1067.

MacroGenics Presents Updated Data from Phase 1 Study of Margetuximab at ASCO Annual Meeting 2015. May 30, 2015; pp. 1-2.

McCann, A. et al. (1990) "c-erbB-2 Oncoprotein Expression In Primary Human Tumors," Cancer 65:88-92.

Perez, E.A., et al. (2014) "HER2 testing: Current Status and Future Directions," Cancer Treatment Reviews, 40:276-284.

Rugo, H.S. et al. (2021) "SOPHIA Study Group. Efficacy of Margetuximab vs Trastuzumab in Patients With Pretreated ERBB2-Positive Advanced Breast Cancer: A Phase 3 Randomized Clinical Trial," JAMA Oncol. Apr. 1, 2021;7(4):573-584.

Rugo, H.S., et al. (2019) "SOPHIA Primary PFS Analysis: A Phase 3 Study of Margetuximab + Chemotherapy vs Trastuzumab + Chemotherapy in Patients With HER2+ Metastatic Breast Cancer After Prior Anti-HER2 Therapies," J. Clin. Oncol. 37:15_suppl, 1000 (2019 ASCO Meeting); 21 pages.

Salkeni, M.A. et al. (2021) "Neu Perspectives, Therapies, and Challenges for Metastatic HER2-Positive Breast Cancer. Breast Cancer," Dove Med Press 13:539-557.

Slamon, D.J. et al. (1987) "Human Breast Cancer: Correlation Of Relapse And Survival With Amplification Of The HER-2/neu Oncogene," Science 235:177-182.

Slamon, D.J. et al. (1989) "Studies of the HER2/neu proto-oncogene in Human Breast and Ovarian Cancer," Science 244:707-712.

Vogel, C.L. et al. (2001) "First-Line Herceptin® Monotherapy in Metastatic Breast Cancer," Oncol. 61:37-42.

Vogel, C.L. et al. (2002) "Efficacy And Safety Of Trastuzumab As A Single Agent In First-Line Treatment Of HER2-Overexpressing Metastatic Breast Cancer," J. Clin. Oncol. 20(3):719-726.

WHO Drug Information, 2014, Recommended INN: List 70, 28(1):93-94.

Xu, M. et al. (2012) "The Tumor Immunosuppressive Microenvironment Impairs The Therapy Of Anti-Her2/neu Antibody," Protein Cell 3(6):441-449.

Yonemura, Y. et al. (1991) "Evaluation Of Immunoreactivity For erbB-2 Protein As A Marker Of Poor Short Term Prognosis In Gastric Cancer" Cancer Research 51:1034.

Awwad, S. et al. (2018) "Overview of Antibody Drug Delivery," Pharmaceutics 10(3):83:1-24.

Bang, J.Y. et al. (2017) "First-In-Human Phase 1 Study Of Margetuximab (MGAH22), An 1-5, 32-34 Fc-Modified Chimeric Monoclonal Antibody, In Patients With HER2-Positive Advanced Solid Tumors," Annals of Oncology 28(4):855-861.

Daugherty, A.L. et al. (2006) "Formulation And Delivery Issues For Monoclonal Antibody Therapeutics," Adv. Drug Deliv. Rev. 58(5-6):686-706.

Daugherty, A.L. et al. (2009) "Formulation And Delivery Issues For Monoclonal Antibody Therapeutics," Current Trends in Monoclonal Antibody Development and Manufacturing, Biotechnology: Pharmaceutical Aspects (Edited by: S.J. Shire et al.) American Association of Pharmaceutical Scientists; pp. 103-129.

Jena Bioscience GmbH "Screen Formulation For final 1x buffer FORMOscreen(R) Antibody 1-5, 32-34 Formulation Screen," Product information sheet (online) Jul. 1, 2020 [URL:Https://www.jenabioscience.com/images/0f4b2c43de/CS-360_FORM0screen_formulation.pdf]; pp. 1-4.

Kayser, V. et al. (2011) "Conformational Stability And Aggregation Of Therapeutic Monoclonal Antibodies Studied With ANS And Thioflavin T Binding," mAbs 2011, 3, 408-411.

PCT International Search Report PCT/US21/61553 (2022); 4 pages.

PCT International Search Report PCT/US21/61553 (2022) Search History; 5 pages.

PCT Written Opinion PCT/US21/61553 (2022); 5 pages.

Sifniotis, V. et al. (2019) "Current Advancements in Addressing Key Challenges of Therapeutic Antibody Design, Manufacture, and Composition," Antibodies (Basel). 8(2):36:1-23.

Vázquez-Rey, M. et al. (2011) "Aggregates In Monoclonal Antibody Manufacturing Processes," Biotechnol. Bioeng. 108(7):1494-1508.

Wang, W. et al. (2007) "Antibody Structure, Instability, And Formulation," J. Pharm. Sci. 96(1):1-26.

\* cited by examiner

PHARMACEUTICAL COMPOSITIONS OF A HER2/NEU ANTIBODY AND USE OF THE SAME

CROSS REFERENCE TO RELATED APPLICATIONS

This application is a continuation application of, and claims priority to, US Patent Application Serial No. PCT/US21/61553 (filed Dec. 2, 2021; pending), and claims priority to U.S. Patent Application Ser. Nos. 63/233,588 (filed Aug. 16, 2021), 63/174,766 (filed on Apr. 14, 2021), and 63/121,279 (filed on Dec. 4, 2020), each of which applications are herein incorporated by reference in their entirety.

REFERENCE TO SEQUENCE LISTING

This application includes one or more Sequence Listings pursuant to 37 C.F.R. 1.821 et seq., which are disclosed in computer-readable media (file name: 1301_0168PCT-US1_ST25.txt, created on Dec. 3, 2021, and having a size of 6,437 bytes), which file is incorporated herein in its entirety.

FIELD OF THE INVENTION

The present invention is directed in part to pharmaceutical compositions for storage and administration comprising a) a HER2/neu antibody ("margetuximab"), b) buffering agents, and c) stabilizers, wherein said margetuximab is stable. In invention in part provides, containers and kits comprising such pharmaceutical compositions. The invention is directed in part to the use of such pharmaceutical compositions, containers, and kits containing margetuximab in the treatment of a cancer, and in certain aspects, treatment of a HER2/neu-positive (HER2$^+$) cancer (i.e., cancer that expresses HER2), including breast cancer or gastric cancer or gastroesophageal junction cancer.

BACKGROUND OF THE INVENTION

HER2/neu is an important member of the ErbB family. It is a 185 kDa receptor protein that was originally identified as the product of the ERBB2 transforming gene from neuroblastomas of chemically treated rats. HER2/neu functions as a growth factor receptor and is often overexpressed by many types of cancer cells including breast cancers, ovarian cancers, carcinomas of the stomach, endometrium, salivary gland, lung, kidney, colon, thyroid, pancreas and bladder caners, and its overexpression is associated with aggressive clinical progression and poor prognosis in affected patients (see e.g., Slamon, D. J. et al. (1987) "*Human Breast Cancer: Correlation Of Relapse And Survival With Amplification Of The HER-2/neu Oncogene,*" Science 235:177-182; McCann, A. et al. (1990) "*c-erbB-2 Oncoprotein Expression In Primary Human Tumors,*" Cancer 65:88-92; Yonemura, Y. et al. (1991) "*Evaluation Of Immunoreactivity For erbB-2 Protein As A Marker Of Poor Short Term Prognosis In Gastric Cancer*" Cancer Research 51:1034).

The role of HER2/neu in numerous cancers has prompted the development and use of HER2/neu binding molecule, particularly, anti-HER2/neu antibodies, for the treatment of HER2/neu expressing tumors. A humanized antibody known as "trastuzumab" (HERCEPTIN®, CAS No. 180288-69-1), was developed and has been approved for treating cancers that involve the overexpression or gene amplification of HER2/neu, including breast cancer (Cobleigh, M. A. et al. (1999) "*Multinational Study Of The Efficacy And Safety Of Humanized anti-HER2 Monoclonal Antibody In Women Who Have HER2-Overexpressing Metastatic Breast Cancer That Has Progressed After Chemotherapy For Metastatic Disease,*" J. Clin. Oncol. 17:2639-2648). Another anti-HER2/neu antibody known as "pertuzumab" (PERJETA, CAS No. 380610-27-5) which binds a different epitope, has been approved for treating cancers in combination with trastuzumab (Moya-Homo, I., & Cortés, J. (2015) "*The Expanding Role Of Pertuzumab In The Treatment Of HER2-Positive Breast Cancer,*" Breast Cancer, 7:125-132; Tabernero, J., et al. (2018) "*Pertuzumab Plus Trastuzumab And Chemotherapy For HER2-Positive Metastatic Gastric Or Gastro-Oesophageal Junction Cancer (JACOB): Final Analysis Of A Double-Blind, Randomised, Placebo-Controlled Phase 3 Study,*" The Lancet 19:1372-1384). New and improved forms of anti-HER2/neu antibodies for use in cancer therapies, for example engineered chimeric 4D5 antibodies having, enhanced effector functions, and the like are provided herein and have been described (PCT Publication WO 2009/123894). One such antibody known as "margetuximab" (CAS No1350624-75-7) has recently been reported to provide a greater benefit as compared to trastuzumab (Rugo, H. S., et al. (2019) "*SOPHIA Primary Analysis*" J. Clin. Oncol. 37:15 suppl, 1000).

However, an unmet need remains to develop antibody compositions for patients whose tumors express HER2/neu, including those whose tumors express low levels of HER2/neu or who have failed on other HER2/neu therapies. The present invention directly addresses this need and others, as described below. In particular, the present invention provides pharmaceutical compositions comprising margetuximab. The invention is also directed to the use of such pharmaceutical compositions and pharmaceutical kits that that contain such pharmaceutical compositions for the treatment of HER2/neu-positive (HER2$^+$)cancer (i.e., a cancer that expresses HER2).

SUMMARY OF THE INVENTION

The present invention is directed in part to pharmaceutical compositions for storage and administration comprising a) a HER2/neu antibody ("margetuximab"), b) buffering agents, and c) stabilizers, wherein the margetuximab is stable. In invention in part provides, containers and kits comprising such pharmaceutical compositions. The invention is directed in part to the use of such pharmaceutical compositions, containers, and kits containing margetuximab in the treatment of cancer, and in certain aspects, treatment of HER2/neu-positive (HER2$^+$) cancer (i.e., cancer that expresses HER2), including breast cancer or gastric cancer, or GEJ cancer, for example with a therapeutically effective amount or prophylactically effective amount of margetuximab.

In detail, the invention provides a pharmaceutical composition comprising margetuximab, a sodium phosphate monohydrate, a sodium phosphate dibasic heptahydrate, sodium chloride, L-arginine hydrochloride and sucrose as stabilizers, polysorbate 80 ("PS80") and water. The invention further provides an alternative embodiment of such pharmaceutical compositions, wherein such composition comprises sodium phosphate dibasic anhydrous in place of a sodium phosphate dibasic heptahydrate.

The invention provides the embodiment of such pharmaceutical compositions, wherein margetuximab has a concentration of about 20 mg/mL to about 100 mg/mL. The invention provides the embodiment of such pharmaceutical compositions, wherein margetuximab has a concentration of about 21.25 mg/mL to about 28.75 mg/mL or about 22.5 mg/mL to about 27.5 mg/mL, and particularly wherein the concentration of margetuximab is about 25 mg/mL±2.5 mg/mL.

The invention provides the embodiment of such pharmaceutical compositions, wherein the sodium phosphate monohydrate has a concentration of about 0.94 mg/mL to about 1.27 mg/mL, and particularly wherein the concentration of sodium phosphate monohydrate is about 1.08 mg/mL to about 1.1 mg/mL.

The invention provides the embodiment of such pharmaceutical compositions, wherein the sodium phosphate dibasic heptahydrate has a concentration of about 0.49 mg/mL to about 0.67 mg/mL, and particularly wherein the concentration of sodium phosphate dibasic heptahydrate is about 0.58 mg/mL. The invention further provides an alternative embodiment of such pharmaceutical compositions, wherein the sodium phosphate dibasic anhydrous has a concentration of about 0.22 mg/mL to about 0.30 mg/mL, and particularly wherein the concentration of sodium phosphate dibasic anhydrous is 0.26 mg/mL.

The invention provides the embodiment of such pharmaceutical compositions, wherein the sodium chloride has a concentration of about 2.47 mg/mL to about 3.34 mg/mL, and particularly about 2.9 mg/mL.

The invention provides the embodiment of such pharmaceutical compositions, wherein the L-arginine hydrochloride has a concentration of about 9.35 mg/mL to about 12.75 mg/mL, and particularly wherein the L-arginine hydrochloride has a concentration about 11 mg/mL.

The invention provides the embodiment of such pharmaceutical compositions, wherein the sucrose has a concentration of about 25.5 mg/mL to about 34.5 mg/mL, and particularly wherein the sucrose has a concentration about 30 mg/mL.

The invention provides the embodiment of such pharmaceutical compositions, wherein the PS80 has a concentration of about 0.05 mg/mL to about 0.20 mg/mL, and particularly wherein the PS80 has a concentration about 0.1 mg/mL.

The invention provides the embodiment of such pharmaceutical compositions, wherein the composition has a pH of about 5.8 to about 6.4, and particularly a pH of 6.1±0.3.

The invention provides the embodiment of such pharmaceutical compositions, wherein the composition comprises about 21.25 mg/mL to about 28.75 mg/mL of margetuximab, about 0.94 mg/mL to about 1.27 mg/mL of sodium phosphate monohydrate, about 0.49 mg/mL to about 0.67 mg/mL of sodium phosphate dibasic heptahydrate, about 2.47 mg/mL to about 3.34 mg/mL of sodium chloride, about 9.35 mg/mL to about 12.75 mg/mL of L-arginine hydrochloride, about 25.5 mg/mL to about 34.5 mg/mL of sucrose, about 0.05 mg/mL to about 0.20 mg/mL of PS80, and water, wherein the composition has a pH of about 5.8 to about 6.4. The invention further provides the alternative embodiment of such pharmaceutical compositions, wherein the composition comprises about 21.25 mg/mL to about 28.75 mg/mL of margetuximab, about 0.94 mg/mL to about 1.27 mg/mL of sodium phosphate monohydrate, 0.22 mg/mL to about 0.30 mg/mL of sodium phosphate dibasic anhydrous, about 2.47 mg/mL to about 3.34 mg/mL of sodium chloride, about 9.35 mg/mL to about 12.75 mg/mL of L-arginine hydrochloride, about 25.5 mg/mL to about 34.5 mg/mL of sucrose, about 0.05 mg/mL to about 0.20 mg/mL of PS80, and water, wherein the composition has a pH of about 5.8 to about 6.4.

The invention provides the embodiment of such pharmaceutical compositions, wherein the composition comprises about 22.5 mg/mL to about 27.5 mg/mL of margetuximab, about 0.94 mg/mL to about 1.27 mg/mL of sodium phosphate monohydrate, about 0.49 mg/mL to about 0.67 mg/mL of sodium phosphate dibasic heptahydrate, about 2.47 mg/mL to about 3.34 mg/mL of sodium chloride, about 9.35 mg/mL to about 12.75 mg/mL of L-arginine hydrochloride, about 25.5 mg/mL to about 34.5 mg/mL of sucrose, about 0.05 mg/mL to about 0.20 mg/mL of PS80, and water, wherein the composition has a pH of about 5.8 to about 6.4. The invention further provides the alternative embodiment of such pharmaceutical compositions, wherein the composition comprises about 22.5 mg/mL to about 27.5 mg/mL of margetuximab, about 0.94 mg/mL to about 1.27 mg/mL of sodium phosphate monohydrate, 0.22 mg/mL to about 0.30 mg/mL of sodium phosphate dibasic anhydrous, about 2.47 mg/mL to about 3.34 mg/mL of sodium chloride, about 9.35 mg/mL to about 12.75 mg/mL of L-arginine hydrochloride, about 25.5 mg/mL to about 34.5 mg/mL of sucrose, about 0.05 mg/mL to about 0.20 mg/mL of PS80, and water, wherein the composition has a pH of about 5.8 to about 6.4.

The invention provides the embodiment of such pharmaceutical compositions, wherein about 10 mL of the composition comprises about 25 mg/mL+2.5 mg/mL of margetuximab, about 1.1 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, about 0.1 mg/mL PS80, and water, wherein the composition has a pH of 6.1±0.3. The invention further provides the alternative embodiment of such pharmaceutical compositions, wherein about 10 mL of the composition comprises 25 mg/mL±2.5 mg/mL of margetuximab, about 1.08 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, about 0.1 mg/mL PS80, and water, wherein the composition has a pH of 6.1±0.3. The invention further provides the alternative embodiment of such pharmaceutical compositions, wherein about 10 mL of the composition comprises 25 mg/mL±2.5 mg/mL of margetuximab, about 1.1 mg/mL sodium phosphate monohydrate, about 0.26 mg/mL of sodium phosphate dibasic anhydrous, about 2.9 mg/mL sodium chloride, about 11 mg/mL L-arginine hydrochloride, about 30 mg/mL sucrose, about 0.1 mg/mL PS80, and water, wherein the composition has a pH of 6.1±0.3. The invention further provides the alternative embodiment of such pharmaceutical compositions, wherein about 10 mL of the composition comprises 25 mg/mL±2.5 mg/mL of margetuximab, about 1.08 mg/mL sodium phosphate monohydrate, about 0.26 mg/mL of sodium phosphate dibasic anhydrous, about 2.9 mg/mL sodium chloride, about 11 mg/mL L-arginine hydrochloride, about 30 mg/mL sucrose, about 0.1 mg/mL PS80, and water, wherein the composition has a pH of 6.1±0.3.

The invention provides the embodiment of such pharmaceutical compositions, wherein about 10 mL of the composition comprises 25 mg/mL±2.5 mg/mL of margetuximab, about 1.1 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, about 0.1 mg/mL PS80, and water, wherein the composition has a pH of 5.8 to 6.4. The invention further provides the alternative embodiment of such pharmaceutical compositions, wherein about 10 mL of the composition comprises 25 mg/mL+2.5 mg/mL of margetuximab, about 1.08 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, about 0.1 mg/mL PS80, and water, wherein the composition has a pH of 5.8 to 6.4. The invention further provides the alternative embodiment of such pharmaceutical compositions, wherein about 10 mL of the composition comprises 25 mg/mL+2.5 mg/mL of margetuximab, about 1.1 mg/mL sodium phosphate monohydrate, about 0.26 mg/mL of sodium phosphate dibasic anhydrous, about 2.9 mg/mL sodium chloride, about 11 mg/mL L-arginine hydrochloride, about 30 mg/mL sucrose, about 0.1 mg/mL PS80, and water, wherein the composition has a pH of 5.8 to 6.4. The invention further provides the alternative embodiment of such pharmaceutical compositions, wherein about 10 mL of the composition comprises 25 mg/mL±2.5 mg/mL of margetuximab, about 1.08 mg/mL sodium phosphate monohydrate, about 0.26 mg/mL of sodium phosphate dibasic anhydrous, about 2.9 mg/mL sodium chloride, about 11 mg/mL L-arginine hydrochloride, about 30 mg/mL sucrose, about 0.1 mg/mL PS80, and water, wherein the composition has a pH of 5.8 to 6.4.

The invention provides the embodiment of such pharmaceutical compositions, wherein the composition is a liquid.

The invention provides a container comprising any of the pharmaceutical compositions disclosed herein. The invention further provides an embodiment of such container, wherein such container comprises about 5 mL to about 20 mL volume of such pharmaceutical compositions. The invention further provides an embodiment of such container, wherein such container comprises about 5 mL volume, about 10 mL volume, about 15 mL volume, or about 20 mL volume of such pharmaceutical compositions.

The invention provides the embodiment of such pharmaceutical compositions, wherein a 10 mL volume of the composition comprises about 250 mg of margetuximab, about 10.8 mg sodium phosphate monohydrate, about 5.8 mg sodium phosphate dibasic heptahydrate, about 29 mg sodium chloride, about 110 mg L-arginine hydrochloride, about 300 mg sucrose, about 1 mg PS80, and water, and wherein the composition has a pH of 6.1±0.3. The invention further provides the alternative embodiment of such pharmaceutical compositions, wherein a 10 mL volume of the composition comprises 250 mg of margetuximab, about 10.8 mg sodium phosphate monohydrate, about 2.6 mg of sodium phosphate dibasic anhydrous, about 29 mg sodium chloride, about 110 mg L-arginine hydrochloride, about 300 mg sucrose, about 1 mg PS80, and water, and wherein the composition has a pH of 6.1±0.3.

The invention provides the embodiment of such pharmaceutical compositions, wherein a 10 mL volume of the composition comprises about 250 mg of margetuximab, about 10.8 mg sodium phosphate monohydrate, about 5.8 mg sodium phosphate dibasic heptahydrate, about 29 mg sodium chloride, about 110 mg L-arginine hydrochloride, about 300 mg sucrose, about 1 mg PS80, and water, and wherein the composition has a pH of 5.8 to 6.4. The invention further provides the alternative embodiment of such pharmaceutical compositions, wherein a 10 mL volume of the composition comprises 250 mg of margetuximab, about 10.8 mg sodium phosphate monohydrate, about 2.6 mg of sodium phosphate dibasic anhydrous, about 29 mg sodium chloride, about 110 mg L-arginine hydrochloride, about 300 mg sucrose, about 1 mg PS80, and water, and wherein the composition has a pH of 5.8 to 6.4.

The invention provides the embodiment of such pharmaceutical compositions, wherein the composition has an osmolality of about 270-330 mOsm/kg $H_2O$, about 275-325 mOsm/kg $H_2O$, about 290-315 mOsm/kg $H_2O$, and particularly about 300 mOsm/kg $H_2O$.

The invention provides the embodiment of such pharmaceutical compositions, wherein margetuximab comprises a HER2/neu Binding Domain comprising a Heavy Chain Variable Domain ($VH_{HER2}$) having the amino acid sequence of SEQ ID NO:1 and a Light Chain Variable Domain ($VL_{HER2}$) having the amino acid sequence of SEQ ID NO:2, wherein: the Light Chain Variable Domain ($VL_{HER2}$) comprises the $CDR_L1$, $CDR_L2$ and $CDR_L3$ of margetuximab and the Heavy Chain Variable Domain ($VH_{HER2}$) comprises the $CDR_H1$, $CDR_H2$ and $CDR_H3$ of margetuximab. The invention further provides the embodiment of such pharmaceutical compositions, wherein margetuximab comprises a heavy chain having the amino acid sequence of SEQ ID NO:1 and a light chain having the sequence of SEQ ID NO:2.

The invention provides a container comprising any of the above-described pharmaceutical compositions, and particularly, wherein such container is a vial that is aseptically filled.

The invention further provides a container comprising a nominal 5 mL to 20 mL volume of any of the above-described pharmaceutical compositions, and particularly, wherein such composition is a liquid and the container is a vial that is aseptically filled.

The invention further provides a container comprising a nominal 10 mL volume of any of the above-described pharmaceutical compositions, and particularly, wherein such composition is a liquid and the container is a vial that is aseptically filled.

The invention provides the embodiment of such container, wherein the 10 mL volume of the liquid comprises:
a) about 250 mg margetuximab;
b) about 10.8 mg to about 11 mg sodium phosphate monohydrate;
c) about 5.8 mg sodium phosphate dibasic heptahydrate;
d) about 29 mg sodium chloride;
e) about 110 mg L-arginine hydrochloride;
f) about 300 mg sucrose;
g) about 1 mg PS80; and
h) water; and
wherein the composition has a pH of 6.1±0.3.

The invention provides the embodiment of such container, wherein the 10 mL volume of the liquid comprises:
i) about 250 mg margetuximab;
j) about 10.8 mg to about 11 mg sodium phosphate monohydrate;
k) about 5.8 mg sodium phosphate dibasic heptahydrate;
l) about 29 mg sodium chloride;
m) about 110 mg L-arginine hydrochloride;
n) about 300 mg sucrose;
o) about 1 mg PS80; and
p) water; and
wherein the composition has a pH of 5.8 to 6.4.

The invention provides the embodiment of such pharmaceutical compositions wherein the composition maintains monomeric purity of margetuximab for at least about 3 months at 25° C.

The invention provides the embodiment of such pharmaceutical compositions, wherein the composition maintains monomeric purity of margetuximab for at least about 18 months at 2-8° C. The invention further provides the embodiment of such pharmaceutical compositions, wherein the composition maintains monomeric purity of margetuximab for at least about 24 months at 2-8° C. The invention further provides the embodiment of such pharmaceutical compositions, wherein the composition maintains monomeric purity of margetuximab for about 36 months at 2-8° C.

The invention provides an embodiment of such pharmaceutical compositions, wherein the composition maintains the charge heterogeneity profile of the margetuximab for about for at least about 3 months at 25° C. The invention further provides an embodiment of such pharmaceutical compositions, wherein the composition maintains the charge heterogeneity profile of the margetuximab for about for at least about 36 months at about 2-8° C.

The invention provides the embodiment of such pharmaceutical compositions, wherein the compositions have a shelf-life of at least about 18 months at 2-8° C. The invention further provides the embodiment of such pharmaceutical compositions, wherein the compositions have a shelf-life of about 36 months at 2-8° C.

The invention provides the embodiment of such pharmaceutical compositions, wherein the compositions have a shelf-life of at least about 3 months at 25° C.

The invention provides the embodiment of such pharmaceutical compositions, wherein the composition is sterile.

The invention provides a container comprising such pharmaceutical compositions, particularly an aseptically filled vial comprising such pharmaceutical compositions.

The invention additionally provides a sealed package comprising any of the above-described pharmaceutical compositions, or any of the above-described containers.

The invention provides a sealed package comprising one vial comprising about 10 mL volume of any of the above-described pharmaceutical compositions.

The invention provides a sealed package comprising four vials, each comprising about 10 mL volume of any of the above-described pharmaceutical compositions.

The invention provides a kit comprising any of the above-described pharmaceutical compositions, containers, or sealed packages, and optionally further comprising instructions for administration of the pharmaceutical composition to a subject in need thereof.

The invention additionally provides a kit comprising:
a) a container comprising a pharmaceutical composition, the composition comprising about 21.25 mg/mL to about 28.75 mg/mL of margetuximab, about 0.94 mg/mL to about 1.27 mg/mL of sodium phosphate monohydrate, about 0.49 mg/mL to about 0.67 mg/mL of sodium phosphate dibasic heptahydrate, about 2.47 mg/mL to about 3.34 mg/mL of sodium chloride, about 9.35 mg/mL to about 12.75 mg/mL of L-arginine hydrochloride, about 25.5 mg/mL to about 34.5 mg/mL of sucrose and about 0.05 mg/mL to about 0.20 mg/mL of PS80, and water, wherein the composition has a pH of about 5.8 to about 6.4.; and
b) instructions for administration of the pharmaceutical composition to a subject in need thereof.

The invention provides a kit comprising:
a) a container comprising a pharmaceutical composition, wherein 10 mL of the composition comprises 25 mg/mL±2.5 mg/mL of margetuximab, about 1.08 mg/mL to about 1.1 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, and about 0.1 mg/mL PS80, and water, wherein the composition has a pH of 6.1±0.3; and
b) instructions for administration of the pharmaceutical composition to a subject in need thereof.

The invention provides a kit comprising:
a) a container comprising a pharmaceutical composition, wherein 10 mL of the composition comprises 25 mg/mL±2.5 mg/mL of margetuximab, about 1.08 mg/mL to about 1.1 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, and about 0.1 mg/mL PS80, and water, wherein the composition has a pH of 5.8 to 6.4; and
b) instructions for administration of the pharmaceutical composition to a subject in need thereof.

The invention provides a kit comprising:
a) a container comprising a pharmaceutical composition, wherein 10 mL of the composition comprises about 250 mg of margetuximab, about 10.8 mg sodium phosphate monohydrate, about 5.8 mg sodium phosphate dibasic heptahydrate, about 29 mg sodium chloride, about 110 mg L-arginine hydrochloride, about 300 mg sucrose, about 1 mg PS80, and water, and wherein the composition has a pH of 6.1±0.3; and
b) instructions for administration of the pharmaceutical composition to a subject in need thereof.

The invention provides a kit comprising:
a) a container comprising a pharmaceutical composition, wherein 10 mL of the composition comprises about 250 mg of margetuximab, about 10.8 mg sodium phosphate monohydrate, about 5.8 mg sodium phosphate dibasic heptahydrate, about 29 mg sodium chloride, about 110 mg L-arginine hydrochloride, about 300 mg sucrose, about 1 mg PS80, and water, and wherein the composition has a pH of 5.8 to 6.4; and
b) instructions for administration of the pharmaceutical composition to a subject in need thereof.

The invention provides the embodiment of such pharmaceutical compositions, containers, sealed packages, or kits wherein the water is sterile, nonpyrogenic, distilled water. The invention further provides the embodiment of such pharmaceutical compositions, containers, sealed packages or kits wherein the water is Water for Injection, USP, or the equivalent.

The invention additionally provides the embodiment of such kits, wherein the subject is a human patient.

The invention additionally provides a sealed package comprising any of the above-described pharmaceutical compositions, containers, or kits, and optionally instructions for storage and/or use of such kit, for administration of the pharmaceutical composition to a subject in need thereof.

The invention additionally provides the embodiment of such kits, wherein the instructions provide that margetuximab is administered by intravenous (IV) infusion over about 120 minutes.

The invention additionally provides the embodiment of such kits, wherein margetuximab is administered by IV infusion over about 30 minutes.

The invention additionally provides the embodiment of such kits wherein the instructions provide that such pharmaceutical composition is diluted in 0.9% sodium chloride for IV infusion.

The invention provides a method of treating cancer, comprising administering margetuximab to a subject in need thereof using any of the disclosed pharmaceutical compositions, any of the disclosed containers, any of the disclosed sealed packages, or any of the disclosed kits.

The invention additionally provides a method of administering a pharmaceutical composition of the invention to a subject in need thereof using one of the above-described pharmaceutical compositions, sealed packages or kits, wherein in the method comprises:
a) diluting the pharmaceutical composition in a container in 0.9% sodium chloride to obtain a dosing solution;
b) inverting the container to mix the diluted solution; and
c) attaching the container containing the dosing solution to a device for administration to the subject.

The invention additionally provides the embodiment of such methods of administering wherein the container is an IV bag containing 0.9% sodium chloride.

The invention additionally provides the embodiment of such methods of administering wherein the dosing solution maintains monomeric purity of the margetuximab for about 24 hours at 25° C. or for about 24 hours at 2-8° C.

The invention additionally provides the embodiment of such methods of administering, wherein the administration of the dosing solution is by IV infusion for at least about 120 minutes.

The invention additionally provides the embodiment of such methods of administering, wherein the administration of the dosing solution is by IV infusion for at least about 60 minutes.

The invention additionally provides the embodiment of such methods of administering, wherein the administration of the dosing solution is by IV infusion for at least about 30 minutes.

The invention additionally provides the embodiment of such methods of administering, wherein the pharmaceutical composition is diluted to obtain a treatment dosage of about 15 mg/kg of margetuximab in the dosing solution.

The invention additionally provides the embodiment of such methods of administering, wherein for one or more subsequent doses, the pharmaceutical composition comprising margetuximab dosing solution is administered once every 3 weeks.

The invention additionally provides the embodiment of such methods of administering, wherein the patient is a human subject.

The invention provides the embodiment of such methods of administering, wherein the patient is suffering from cancer, and in some embodiments, a HER2$^+$ cancer (i.e., a cancer that expresses HER2).

The invention provides the embodiment of such methods of administering, wherein the cancer is breast cancer, metastatic breast cancer, cervical cancer, colorectal cancer, endometrial cancer, gastric cancer, GEJ cancer, or ovarian cancer, and particularly wherein the cancer is, HER2$^+$ breast cancer, HER2$^+$ metastatic breast cancer, HER2$^+$ cervical cancer, HER2$^+$ colorectal cancer, HER2$^+$ endometrial cancer, HER2$^+$ gastric cancer, HER2$^+$ GEJ cancer, or HER2$^+$ ovarian cancer.

The invention additionally provides a method of treating cancer using any of the above-described pharmaceutical compositions, containers, sealed packages, kits, or methods for administration.

The invention provides a use of any of the above-described pharmaceutical compositions, containers, sealed packages, or kits for the treatment of cancer in a subject in need thereof.

The invention also provides the embodiment of such uses, wherein the use comprises:
a) diluting the pharmaceutical composition in a container in 0.9% sodium chloride to obtain a dosing solution;
b) inverting the container to mix the diluted solution; and
c) attaching the container containing the dosing solution to a device for administration to the subject.

The invention additionally provides the embodiment of such uses of administering wherein the container is an IV bag containing 0.9% sodium chloride.

The invention additionally provides the embodiment of such uses of administering wherein the dosing solution maintains monomeric purity of the margetuximab for about 24 hours at 25° C. or for about 24 hours at 2-8° C.

The invention additionally provides the embodiment of such uses of administering, wherein the administration of the dosing solution is by IV infusion for at least about 120 minutes.

The invention additionally provides the embodiment of such uses of administering, wherein the administration of the dosing solution is by IV infusion for at least about 60 minutes.

The invention additionally provides the embodiment of such uses of administering, wherein the administration of the dosing solution is by IV infusion for at least about 30 minutes.

The invention additionally provides the embodiment of such uses of administering, wherein the pharmaceutical composition is diluted to obtain a treatment dosage of about 15 mg/kg of margetuximab in the dosing solution.

The invention additionally provides the embodiment of such uses of administering, wherein for one or more subsequent doses, the pharmaceutical composition comprising margetuximab dosing solution is administered once every 3 weeks.

The invention additionally pertains to the use of the above-described pharmaceutical compositions, containers, sealed packages, kits, or methods for administration for the treatment of a cancer, particularly a HER2$^+$ cancer (i.e., a cancer that expresses HER2).

The invention additionally pertains to the use of such pharmaceutical compositions, containers, sealed packages, kits, or methods for administration, wherein the cancer is breast cancer, metastatic breast cancer, cervical cancer, colorectal cancer, endometrial cancer, gastric cancer, GEJ cancer, or ovarian cancer, and particularly wherein the cancer is HER2$^+$ breast cancer, HER2$^+$ metastatic breast cancer, HER2$^+$ cervical cancer, HER2$^+$ colorectal cancer, HER2$^+$ endometrial cancer, HER2$^+$ gastric cancer, HER2$^+$ GEJ cancer, or HER2$^+$ ovarian cancer.

The invention particularly pertains to the use, wherein the subject is a human subject.

DETAILED DESCRIPTION OF THE INVENTION

The present invention is directed in part to pharmaceutical compositions for storage and administration comprising a) a HER2/neu antibody ("margetuximab"), b) buffering agents, and c) a stabilizers, wherein the margetuximab is stable. In invention in part provides, containers and kits comprising such pharmaceutical compositions. The invention is directed in part to the use of such pharmaceutical compositions, containers, and kits containing margetuximab in the treatment of cancer, and in certain aspects, treatment of a HER2/neu-positive (HER2$^+$) cancer (i.e., a cancer that expresses HER2), including breast cancer or gastric cancer or GEJ cancer, for example with a therapeutically effective amount or prophylactically effective amount of margetuximab.

I. Margetuximab

Margetuximab (also known as MGAH22; CAS Reg No. 1350624-75-7, see, for example, U.S. Pat. No. 8,802,093) is a chimeric Fc-optimized monoclonal antibody that binds to HER2/neu and mediates enhanced ADCC activity. Trastuzumab (also known as rhuMAB4D5, and marketed as HERCEPTIN®; CAS Reg No 180288-69-1; see, U.S. Pat. No. 5,821,337) is a humanized antibody, having wild-type IgG1/kappa constant regions. The Fc domain of margetuximab was modified at 5 sites with the following amino acid changes: L235V, F243L, R292P, Y300L and P396L, wherein the numbering of the residues in an IgG heavy chain is that of the EU index as in Kabat (Kabat, *Sequences Of Proteins Of Immunological Interest* (National Institutes of Health, Bethesda, Md., 1987 and 1991), and refers to the numbering of the human IgG1 EU antibody. The amino acid sequences of the heavy and light chains of margetuximab are presented below (also see, WHO Drug Information, 2014, Recommended INN: List 70, 28(1):93-94). The CDRs as defined by Kabat are underlined.

The amino acid sequence of the Heavy Chain of margetuximab is (SEQ ID NO:1) (CDR$_H$ residues are shown underlined; the constant region is shown with double underline):

```
QVQLQQSGPE LVKPGASLKL SCTASGFNIK

DTYIHWVKQR PEQGLEWIGR

IYPTNGYTRY DPKFQDKATI TADTSSNTAY

LQVSRLTSED TAVYYCSRWG

GDGFYAMDYW GQGASVTVSS ASTKGPSVFP

LAPSSKSTSG GTAALGCLVK

DYFPEPVTVS WNSGALTSGV HTFPAVLQSS

GLYSLSSVVT VPSSSLGTQT

YICNVNHKPS NTKVDKRVEP KSCDKTHTCP

PCPAPELVGG PSVFLLPPKP

KDTLMISRTP EVTCVVVDVS HEDPEVKFNW

YVDGVEVHNA KTKPPEEQYN

STLRVVSVLT VLHQDWLNGK EYKCKVSNKA

LPAPIEKTIS KAKGQPREPQ

VYTLPPSRDE LTKNQVSLTC LVKGFYPSDI

AVEWESNGQP ENNYKTTPLV

LDSDGSFFLY SKLTVDKSRW QQGNVFSCSV

MHEALHNHYT QKSLSLSPGK
```

The amino acid sequence of the Light Chain of margetuximab is (SEQ ID NO:2) (CDR$_L$ residues are shown underlined, the constant region is shown with double underline):

```
DIVMTQSHKF MSTSVGDRVS ITCKASQDVN

TAVAWYQQKP GHSPKLLIYS

ASFRYTGVPD RFTGSRSGTD FTFTISSVQA

EDLAVYYCQQ HYTTPPTFGG

GTKVEIKRTV AAPSVFIFPP SDEQLKSGTA

SVVCLLNNFY PREAKVQWKV
```

```
DNALQSGNSQ ESVTEQDSKD STYSLSSTLT

LSKADYEKHK VYACEVTHQG

LSSPVTKSFN RGEC
```

II. Pharmaceutical Compositions

The pharmaceutical compositions of the invention comprise margetuximab, buffering agents and stabilizers, and are also referred herein as "margetuximab compositions".

As used herein, "about" will be understood by persons of ordinary skill in the art and will vary to some extent depending upon the context in which it is used. As used herein, the term "about" refers to a standard deviation of ±5%, except with respect to weight-based dosage where the term "about" refers to a standard deviation of ±10%.

As used herein, the singular forms "a," "an" and "the" include plural referents unless the context clearly dictates otherwise. Thus, for example, reference to "a" component includes aspects having two or more such components, unless the context clearly indicates otherwise. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

The term "and/or" shall also be interpreted to be inclusive (e.g., "x and/or y" means one or both x or y). In situations where "and/or" or "or" are used as a conjunction for a group of three or more items, the group should be interpreted to include one item alone, all the items together, or any combination or number of the items. Moreover, terms used in the specification and claims such as have, having, include, and including should be construed to be synonymous with the terms comprise and comprising. Other elements may optionally be present other than the elements specifically identified by the "and/or" clause, whether related or unrelated to those elements specifically identified. As a non-limiting example, a reference to "X and/or Y" may refer, in one embodiment, to X only (optionally including elements other than Y); in some embodiments, to Y only (optionally including elements other than X); in yet some embodiments, to both X and Y (optionally including other elements).

As used herein, the term "aqueous" refers to a water containing solution.

As used herein, the term "stable" refers to margetuximab substantially retaining its physical stability, chemical stability, pharmaceutical activity, and/or its biological activity upon storage. The present invention provides pharmaceutical compositions that substantially retain the physical and chemical stability, of margetuximab as well as its biological activity upon storage. In one embodiment, at least 90%, at least 80%, at least 70%, or at least 60% of the physical stability, chemical stability, and/or biological activity is retained during storage.

The term "shelf-life" refers to the period of time during which said pharmaceutical compositions may be stored, in which physical stability, chemical stability, pharmaceutical activity, and/or biological stability are/is substantially retained.

As will be understood by one skilled in the art, for any and all purposes, particularly in terms of providing a written description, all ranges disclosed herein also encompass any and all possible subranges and combinations of subranges thereof, inclusive of the endpoints. As such, all disclosed ranges are to be understood to encompass and provide support for claims that recite any and all subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like, include the number recited and refer to ranges which may be subsequently broken down into subranges as discussed herein. Further, as will be understood by one skilled in the art, a range includes each individual member. Thus, for example, a group having 1-3 layers refers to groups having 1, 2, or 3 layers. Similarly, a group having 1-5 layers refers to groups having 1, 2, 3, 4, or 5 layers, and so forth.

The embodiments illustratively disclosed herein may suitably be practiced in the absence of any element or elements, limitation or limitations not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

Definitions that are contained in text incorporated by reference are excluded to the extent that they contradict definitions in this disclosure.

In one embodiment, during the shelf-life time period, at least 90%, at least 80%, at least 70%, or at least 60%, about 90% or more, about 80% or more, 70% or more, or about 60% or more of the physical stability, chemical stability, and/or biological activity is retained. The shelf-life of a pharmaceutical composition is generally selected based on the period of time a molecule is stable in such composition. In one embodiment, the shelf-life of a pharmaceutical composition is at least about 1 month 25° C., at least about 2 months at 25° C., at least about 3 months at about 25° C., at least about 4 months at 25° C., at least about 6 months at 25° C., at least about 6 months at 2-8° C., at least about 12 months at 2-8° C., at least about 18 months at 2-8° C., at least about 24 months at 2-8° C., at least about 30 months 2-8° C., at least about 36 months 2-8° C., or more than about 36 months at 2-8° C. In one embodiment, the shelf-life of a pharmaceutical composition is at least about 3 months at 25° C. In another embodiment, the shelf-life of a pharmaceutical composition is at least about 18 months at 2-8° C. In another embodiment, the shelf-life of a pharmaceutical composition is at least about 36 months at 2-8° C.

One measure of physical and chemical stability is the monomeric purity of margetuximab in a pharmaceutical composition or in a dosing solution. In one embodiment, the loss of monomeric purity of margetuximab in a pharmaceutical composition or in a dosing solution is less than about 15%, or less than about 10%, or less than about 5%, or less than about 4%, or less than about 3%, or less than about 2%, or less than about 1%, or less than about 0.6%, or less than about 0.4%, or less than about 0.2%, about 15% or less, or about 10% or less, or about 5% or less, or about 4% or less, or about 3% or less, or about 2% or less, about 1% or less, about 0.6% or less, about 0.4% or less or about 0.2% or less over the indicated period of time. In one embodiment, the loss of monomeric purity of margetuximab in a pharmaceutical composition or in a dosing solution is about 5% or less over the indicated period of time. In another embodiment, the loss of monomeric purity of margetuximab in a pharmaceutical composition or in a dosing solution is less than about 4% over the indicated period of time. In another embodiment, the loss of monomeric purity of margetuximab in a pharmaceutical composition or in a dosing solution is about 3% or less over the indicated period of time. In another embodiment, the loss of monomeric purity of margetuximab in a pharmaceutical composition or in a dosing solution is about 2% or less over the indicated period of time. In another embodiment, the loss of monomeric purity of margetuximab in a pharmaceutical composition or in a dosing solution is about 1% or less over the indicated period of time. In certain embodiments, the BMW and/or LMW species of the margetuximab in the composition is measured via size exclusion chromatography (SE-HPLC).

In other embodiments, the monomeric purity of margetuximab in a pharmaceutical composition is maintained for at least about 1 month 25° C., at least about 2 months at 25° C., at least about 3 months at about 25° C., at least about 4 months at 25° C., at least about 6 months at 25° C., at least about 6 months at 2-8° C., at least about 12 months at 2-8° C., at least about 18 months at 2-8° C., at least about 24 months at 2-8° C., at least about 30 months 2-8° C., at least about 36 months 2-8° C., or more than about 36 months at 2-8° C. In one embodiment, monomeric purity of margetuximab in a pharmaceutical composition is maintained at least about 3 months at 25° C. In another embodiment, monomeric purity of margetuximab in a pharmaceutical composition is maintained at least about 18 months at 2-8° C. In another embodiment, monomeric purity of margetuximab in a pharmaceutical composition is maintained at least about 24 months at 2-8° C. In another embodiment, the monomeric purity of margetuximab in a pharmaceutical composition is maintained for about 36 months at 2-8° C. Another measure of stability is the stability of the charge heterogeneity profile of margetuximab in pharmaceutical compositions of the invention or in dosing solutions of the invention. Protein compositions may comprise a variety of variants that differ in their isoelectric point (pI). Such variants are referred to as charge variants. Thus, the charge heterogeneity profile can be determined by measuring the main charge peak (MCP), the acidic variants (AV), and the basic variants (BV) by any suitable method. For example, a margetuximab composition of the invention can comprise MCP, AV and BV components, and changes to the charge heterogeneity profile may be measured by determining the loss of the MCP and/or the accumulation of AV, and/or BV after the indicated time. In one embodiment, the decrease in the MCP of margetuximab in a pharmaceutical composition of the invention or in a dosing solution of the invention is about 15% or less, or about 10% or less, or about 5% or less, or about 4% or less, or about 3% or less, or about 2% or less, or about 1% or less, over the indicated period of time. In one embodiment, the increase in the AV of margetuximab in a pharmaceutical composition of the invention or in a dosing solution of the invention is about 15% or less, or about 10% or less, or about 5% or less, or about 4% or less, or about 3% or less, or about 2% or less, or about 1% or less, over the indicated period of time. In another embodiment, the increase in the BV of margetuximab in a pharmaceutical composition of the invention or in a dosing solution of the invention is about 15% or less, or about 10% or less, or about 5% or less, or about 4% or less, or about 3% or less, or about 2% or less, or about 1% or less, over the indicated period of time. In another embodiment, the decrease in the MCP of margetuximab in a pharmaceutical composition of the invention or in a dosing solution of the invention is about 7% or less over the indicated period of time. In another embodiment, the decrease in the MCP of margetuximab in a pharmaceutical composition of the invention or in a dosing solution of the invention is about 6% or less over the indicated period of time. In another embodiment, the decrease in the MCP of margetuximab in a pharmaceutical composition of the invention or in a dosing solution of the invention is about 5% or less over the indicated period of time. In another embodiment, the increase in the AV of margetuximab in a pharmaceutical composition of the invention or in a dosing solution of the invention is about 7% or less over the indicated period of time. In another embodiment, the increase in the AV of margetuximab in a pharmaceutical composition of the invention or in a dosing solution of the invention is about 6% or less over the indicated period of time. In another embodiment, the increase in the AV of margetuximab in a pharmaceutical composition of the invention or in a dosing solution of the invention is about 5% or less over the indicated period of time. In another embodiment, the increase in the BV of margetuximab in a pharmaceutical composition of the invention or in a dosing solution of the invention is about 4% or less over the indicated period of time. In another embodiment, the increase in the BV of margetuximab in a pharmaceutical composition of the invention or in a dosing solution of the invention is about 3% or less over the indicated period of time. In another embodiment, the increase in the BV of margetuximab in a pharmaceutical composition of the invention or in a dosing solution of the invention is about 2% or less over the indicated period of time. In certain embodiments, the MCP, AV, and BV of the margetuximab in the pharmaceutical composition of the invention or the dosing solution of the invention is measured via by ion exchange high performance liquid chromatography (IE-HPLC). In certain embodiments, the MCP, AV, and BV of the margetuximab in the pharmaceutical composition of the invention or the dosing solution of the invention is measured via by capillary isoelectric focusing (cIEF).

In other embodiments, the charge heterogeneity profile of margetuximab in a pharmaceutical composition of the invention is maintained for at least about 1 month at about 25° C., at least about 2 months at about 25° C., at least about 3 months at about 25° C., at least about 4 months at about 25° C., at least about 6 months at about 25° C., at least about 6 months at about 2-8° C., at least about 12 months at about 2-8° C., at least about 18 months at about 2-8° C., at least about 24 months at about 2° C. to about 8° C., at least about 30 months about 2-8° C., at least about 36 months about 2-8° C., at least about 48 months, or more than about 48 months at about 2-8° C. In one embodiment, heterogeneity profile of margetuximab in a pharmaceutical composition of the invention is maintained at least about 3 months at about 25° C. In another embodiment, heterogeneity profile of margetuximab in a pharmaceutical composition of the invention is maintained for about 36 months or more at about 2-8° C. In another embodiment, the charge heterogeneity profile of margetuximab in a pharmaceutical composition of the invention is maintained for about 48 months at about 2-8° C.

A. Margetuximab Compositions

Generally, the components of the pharmaceutical compositions (i.e., margetuximab compositions) of the invention are supplied mixed together in unit dosage form, for example, as a liquid composition, in a hermetically sealed container such as a vial, ampoule, or sachet indicating the quantity of active agent. In one embodiment, the pharmaceutical composition is supplied as a liquid solution. Such liquid solution is typically to be stored at between 2° C. and 8° C. in their original containers until ready to be administered, although such liquid solutions may be stored at room temperature (~25° C.) for short periods prior to administration.

In certain embodiments, where the margetuximab composition is to be administered by IV infusion, it can be dispensed with a container, bag, or infusion bottle containing sterile 0.9% sodium chloride (saline). Where the margetuximab composition is administered by injection, 0.9% sodium chloride can be provided so that the ingredients may be mixed prior to administration as detailed herein. Such margetuximab compositions can comprise a prophylactically or therapeutically effective amount of margetuximab.

In one embodiment, a pharmaceutical composition of the invention comprises margetuximab, a sodium phosphate monohydrate, a sodium phosphate dibasic heptahydrate, sodium chloride, L-arginine hydrochloride and sucrose as stabilizers, polysorbate 80 ("PS80") and water. In another embodiment, a pharmaceutical composition of the invention comprises margetuximab, a sodium phosphate monohydrate, sodium phosphate dibasic anhydrous, sodium chloride, L-arginine hydrochloride and sucrose as stabilizers, PS80 and water.

In one embodiment, the pharmaceutical composition of the invention comprises margetuximab at a concentration of about 20 mg/mL to about 100 mg/mL. In another embodiment, the pharmaceutical composition of the invention comprises margetuximab at a concentration of about 21.25 mg/mL to about 28.75 mg/mL or about 22.5 mg/mL to about 27.5 mg/mL. In another embodiment, the pharmaceutical composition of the invention comprises margetuximab at a concentration of 25 mg/mL±2.5 mg/mL. Also contemplated are margetuximab concentrations between any of these values, such as about 30 mg/mL, about 40 mg/mL, about 50 mg/mL, about 80 mg/mL, etc.

In one embodiment, the pharmaceutical composition of the invention comprises sodium phosphate monohydrate at a concentration of about 0.94 mg/mL to about 1.27 mg/mL. In another embodiment, the pharmaceutical composition comprises sodium phosphate monohydrate at a concentration of about 1.1 mg/mL. In another embodiment, the pharmaceutical composition comprises sodium phosphate monohydrate at a concentration of about 1.08 mg/mL. Also contemplated are sodium phosphate monohydrate concentrations between any of these values, such as about 0.95 mg/mL, about 1.0 mg/mL, about 1.2 mg/mL, etc.

In one embodiment, the pharmaceutical composition of the invention comprises sodium phosphate dibasic heptahydrate at a concentration of about 0.49 mg/mL to about 0.67 mg/mL. In another embodiment, the pharmaceutical composition of the invention comprises sodium phosphate dibasic heptahydrate at a concentration of about 0.58 mg/mL. In an alternative embodiment, the pharmaceutical composition of the invention comprises sodium phosphate dibasic anhydrous at a concentration of about 0.22 mg/mL to about 0.30 mg/mL. In another alternative embodiment, the pharmaceutical composition of the invention comprises sodium phosphate dibasic anhydrous at a concentration of about 0.26 mg/mL. Also contemplated are sodium phosphate dibasic heptahydrate concentrations between any of these values, such as about 0.50 mg/mL, about 0.55 mg/mL, about 0.60 mg/mL, etc.

In one embodiment, the pharmaceutical composition of the invention comprises sodium chloride at a concentration of about 2.47 mg/mL to about 3.34 mg/mL. In another embodiment, the pharmaceutical composition of the invention comprises sodium chloride at a concentration of about 2.9 mg/mL. Also contemplated are sodium chloride concentrations between any of these values, such as about 2.50 mg/mL, about 2.75 mg/mL, about 3.0 mg/mL, about 3.25 mg/mL, etc.

In one embodiment, the pharmaceutical composition of the invention comprises L-arginine hydrochloride at a concentration of about 9.35 mg/mL to about 12.75 mg/mL. In another embodiment, the pharmaceutical composition of the invention comprises L-arginine hydrochloride at a concentration about 11 mg/mL. Also contemplated are L-arginine hydrochloride concentrations between any of these values, such as about 9.5 mg/mL, about 10 mg/mL, about 11 mg/mL, about 12 mg/mL, etc.

In one embodiment, the pharmaceutical composition of the invention comprises sucrose at a concentration of about 25.5 mg/mL to about 34.5 mg/mL. In another embodiment, the pharmaceutical composition of the invention comprises sucrose at a concentration about 30 mg/mL. Also contemplated are sucrose concentrations between any of these values, such as about 27 mg/mL, about 30 mg/mL, about 32 mg/mL, etc.

In one embodiment, the pharmaceutical composition of the invention comprises PS80 at a concentration of about 0.05 mg/mL to about 0.20 mg/mL. In another embodiment, the pharmaceutical composition of the invention comprises PS80 at a concentration about 0.1 mg/mL. Also contemplated are PS80 concentrations between any of these values, such as about 0.09 mg/mL, about 0.11 mg/mL, about 0.13 mg/mL, etc.

In one embodiment, the pharmaceutical composition of the invention has a pH of about 5.8 to about 6.4 (i.e., 6.1±0.3) In another embodiment, the pharmaceutical composition of the invention has a pH of 6.1±0.3. Also contemplated are pH amounts between any of these values, such as a pH of about 5.9, a pH of about 6.0, a pH of about 6.2, etc.

In one embodiment, the pharmaceutical composition of the invention comprises about 21.25 mg/mL to about 28.75 mg/mL of margetuximab, about 0.94 mg/mL to about 1.27 mg/mL of sodium phosphate monohydrate, about 0.49 mg/mL to about 0.67 mg/mL of sodium phosphate dibasic heptahydrate, about 2.47 mg/mL to about 3.34 mg/mL of sodium chloride, about 9.35 mg/mL to about 12.75 mg/mL of L-arginine hydrochloride, about 25.5 mg/mL to about 34.5 mg/mL of sucrose, about 0.05 mg/mL to about 0.20 mg/mL of PS80, and water, wherein the composition has a pH of about 5.8 to about 6.4. In another embodiment, the pharmaceutical composition of the invention comprises 25 mg/mL±2.5 mg/mL of margetuximab, about 1.08 mg/mL to about 1.1 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, about 0.1 mg/mL PS80, and water, wherein the composition has a pH of 6.1±0.3. In another embodiment, the pharmaceutical composition of the invention comprises 25 mg/mL±2.5 mg/mL of margetuximab, about 1.08 mg/mL to about 1.1 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, about 0.1 mg/mL PS80, and water, wherein the composition has a pH of 5.8 to 6.4.

In an alternative embodiment, the pharmaceutical composition of the invention comprises about 21.25 mg/mL to about 28.75 mg/mL of margetuximab, about 0.94 mg/mL to about 1.27 mg/mL of sodium phosphate monohydrate, 0.22 mg/mL to about 0.30 mg/mL of sodium phosphate dibasic anhydrous, about 2.47 mg/mL to about 3.34 mg/mL of sodium chloride, about 9.35 mg/mL to about 12.75 mg/mL of L-arginine hydrochloride, about 25.5 mg/mL to about 34.5 mg/mL of sucrose, about 0.05 mg/mL to about 0.20 mg/mL of PS80, and water, wherein the composition has a pH of about 5.8 to about 6.4. In another alternative embodiment, the pharmaceutical composition of the invention comprises 25 mg/mL±2.5 mg/mL of margetuximab, about 1.08 mg/mL to about 1.1 mg/mL sodium phosphate monohydrate, about 0.26 mg/mL of sodium phosphate dibasic anhydrous, about 2.9 mg/mL sodium chloride, about 11 mg/mL L-arginine hydrochloride, about 30 mg/mL sucrose, about 0.1 mg/mL PS80, and water, wherein the composition has a pH of 6.1±0.3. In another alternative embodiment, the pharmaceutical composition of the invention comprises 25 mg/mL±2.5 mg/mL of margetuximab, about 1.08 mg/mL to about 1.1 mg/mL sodium phosphate monohydrate, about 0.26 mg/mL of sodium phosphate dibasic anhydrous, about 2.9 mg/mL sodium chloride, about 11 mg/mL L-arginine hydrochloride, about 30 mg/mL sucrose, about 0.1 mg/mL PS80, and water, wherein the composition has a pH of 5.8 to 6.4.

In one embodiment about 5 mL to about 20 mL of the pharmaceutical composition of the invention can comprise 25 mg/mL+2.5 mg/mL of margetuximab, about 1.1 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, about 0.1 mg/mL PS80, and wherein the composition has a pH of 6.1+0.3. In another embodiment about 5 mL to about 20 mL of the pharmaceutical composition of the invention can comprise 25 mg/mL+2.5 mg/mL of margetuximab, about 1.08 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, about 0.1 mg/mL PS80, and wherein the composition has a pH of 6.1+0.3.

In one embodiment, about 10 mL of the pharmaceutical composition of the invention comprises about 250 mg of margetuximab, about 10.8 mg sodium phosphate monohydrate, about 5.8 mg sodium phosphate dibasic heptahydrate, about 29 mg sodium chloride, about 110 mg L-arginine hydrochloride, about 300 mg sucrose, about 1 mg PS80, and water, and wherein the composition has a pH of 6.1±0.3. In another embodiment, about 10 mL of the pharmaceutical composition of the invention comprises about 250 mg of margetuximab, about 10.8 mg sodium phosphate monohydrate, about 5.8 mg sodium phosphate dibasic heptahydrate, about 29 mg sodium chloride, about 110 mg L-arginine hydrochloride, about 300 mg sucrose, about 1 mg PS80, and water, and wherein the composition has a pH of 5.8 to 6.4.

In an alternative embodiment, about 10 mL of the pharmaceutical composition of the invention comprises 250 mg of margetuximab, about 10.8 mg sodium phosphate monohydrate, about 2.6 mg of sodium phosphate dibasic anhydrous, about 29 mg sodium chloride, about 110 mg L-arginine hydrochloride, about 300 mg sucrose, about 1 mg PS80, and water, and wherein the composition has a pH of 6.1±0.3. In another alternative embodiment, about 10 mL of the pharmaceutical composition of the invention comprises 250 mg of margetuximab, about 10.8 mg sodium phosphate monohydrate, about 2.6 mg of sodium phosphate dibasic anhydrous, about 29 mg sodium chloride, about 110 mg L-arginine hydrochloride, about 300 mg sucrose, about 1 mg PS80, and water, and wherein the composition has a pH of 5.8 to 6.4.

In one embodiment, about 10 mL of the pharmaceutical composition of the invention comprises about 250 mg of margetuximab, about 11 mg sodium phosphate monohydrate, about 5.8 mg sodium phosphate dibasic heptahydrate, about 29 mg sodium chloride, about 110 mg L-arginine hydrochloride, about 300 mg sucrose, about 1 mg PS80, and water, and wherein the composition has a pH of 6.1±0.3. In one embodiment, about 10 mL of the pharmaceutical composition of the invention comprises about 250 mg of margetuximab, about 11 mg sodium phosphate monohydrate, about 5.8 mg sodium phosphate dibasic heptahydrate, about 29 mg sodium chloride, about 110 mg L-arginine hydrochloride, about 300 mg sucrose, about 1 mg PS80, and water, and wherein the composition has a pH of 5.8 to 6.4.

In an alternative embodiment, about 10 mL of the pharmaceutical composition of the invention comprises 250 mg of margetuximab, about 11 mg sodium phosphate monohydrate, about 2.6 mg of sodium phosphate dibasic anhydrous, about 29 mg sodium chloride, about 110 mg L-arginine hydrochloride, about 300 mg sucrose, about 1 mg PS80, and water, and wherein the composition has a pH of 6.1±0.3. In another alternative embodiment, about 10 mL of the pharmaceutical composition of the invention comprises 250 mg of margetuximab, about 11 mg sodium phosphate monohydrate, about 2.6 mg of sodium phosphate dibasic anhydrous, about 29 mg sodium chloride, about 110 mg L-arginine hydrochloride, about 300 mg sucrose, about 1 mg PS80, and water, and wherein the composition has a pH of 5.8 to 6.4.

In one embodiment, the pharmaceutical composition of the invention has an osmolality of about 270-330 mOsm/kg $H_2O$. In another embodiment, the pharmaceutical composition of the invention has an osmolality of about 275-325 mOsm/kg $H_2O$. In another embodiment, the pharmaceutical composition of the invention has an osmolality of about 290-315 mOsm/kg $H_2O$. In another embodiment, the pharmaceutical composition of the invention has an osmolality of about 300 mOsm/kg $H_2O$.

The invention provides the embodiment of such pharmaceutical compositions, sealed packages or kits wherein the water is sterile, nonpyrogenic, distilled water. The invention also provides the embodiment of such pharmaceutical compositions, containers, sealed packages or kits, wherein the water is Water for Injection, USP, or the equivalent.

In one embodiment, the pharmaceutical composition of the invention is a liquid.

In one embodiment, the pharmaceutical composition of the invention is stable for at least about 3 months at 25° C. In another embodiment, the pharmaceutical composition of the invention maintains monomeric purity of margetuximab for at least about 3 months at 25° C. In another embodiment, the loss of monomeric purity of margetuximab in the pharmaceutical composition is about 5% or less over about 3 months at about 25° C. In another embodiment, the loss of monomeric purity of margetuximab in the pharmaceutical composition is about 3% or less over about 3 months at about 25° C. In another embodiment, the pharmaceutical composition of the invention maintains the charge heterogeneity profile of margetuximab for at least about 3 months at about 25° C. In another embodiment, the decrease in the main charge peak (MCP) of margetuximab in the pharmaceutical composition is about 20% or less over about 3 months at about 25° C. In another embodiment, the increase in the AV of margetuximab in the pharmaceutical composition is about 20% or less over about 3 months at about 25° C.

In one embodiment, pharmaceutical composition of the invention is stable for at least about 18 months at 2-8° C. In another embodiment the pharmaceutical composition of the invention maintains monomeric purity of margetuximab for at least about 18 months at 2-8° C. In another embodiment, the loss of monomeric purity of margetuximab in the pharmaceutical composition is about 5% or less over about 18 months at about 2-8° C. In another embodiment, the loss of monomeric purity of margetuximab in the pharmaceutical composition is about 4% or less over about 18 months at about 2-8° C. In another embodiment, the loss of monomeric purity of margetuximab in the pharmaceutical composition is about 3% or less over about 18 months at about 2-8° C. In another embodiment the pharmaceutical composition of the invention maintains the charge heterogeneity profile of margetuximab for at least about 18 months at about 2-8° C. In another embodiment, the decrease in the MCP of margetuximab in the pharmaceutical composition is about 10% or less over about 18 months at about 2-8° C. In another embodiment, the decrease in the MCP of margetuximab in the pharmaceutical composition is about 9% or less over about 18 months at about 2-8° C. In another embodiment, the decrease in the MCP of margetuximab in a pharmaceutical composition or in a dosing solution is about 7% or less over about 18 months at about 2-8° C. In another embodiment, the decrease in the MCP of margetuximab in a pharmaceutical composition or in a dosing solution is about 5% or less over about 18 months at about 2-8° C. In another embodiment, the increase in the AV of margetuximab in the pharmaceutical composition is about 5% or less over about 18 months at about 2-8° C. In another embodiment, the increase in the AV of margetuximab in the pharmaceutical composition is about 4% or less over about 18 months at about 2-8° C. In another embodiment, the increase in the AV of margetuximab in the pharmaceutical composition is about 3% or less over about 18 months at about 2-8° C.

In one embodiment, pharmaceutical composition of the invention is stable for about 36 months at 2-8° C. In another embodiment the pharmaceutical composition of the invention maintains monomeric purity of margetuximab for about 36 months at 2-8° C. In another embodiment, the loss of monomeric purity of margetuximab in the pharmaceutical composition is about 5% or less over about 36 months at about 2-8° C. In another embodiment, the loss of monomeric purity of margetuximab in the pharmaceutical composition is about 4% or less over about 36 months at about 2-8° C. In another embodiment, the loss of monomeric purity of margetuximab in the pharmaceutical composition is about 3% or less over about 36 months at about 2-8° C. In another embodiment the pharmaceutical composition of the invention maintains the charge heterogeneity profile of margetuximab for at least about 36 months at about 2-8° C. In another embodiment, the decrease in the MP of margetuximab in the pharmaceutical composition is about 10% or less over about 36 months at about 2-8° C. In another embodiment, the decrease in the MCP of margetuximab in the pharmaceutical composition is about 9% or less over about 36 months at about 2-8° C. In another embodiment, the decrease in the MCP of margetuximab in the pharmaceutical composition is about 7% or less over about 36 months at about 2-8° C. In another embodiment, the decrease in the MCP of margetuximab in the pharmaceutical composition is about 5% or less over about 36 months at about 2-8° C. In another embodiment, the increase in the AV of margetuximab in the pharmaceutical composition is about 5% or less over about 36 months at about 2-8° C. In another embodiment, the increase in the AV of margetuximab in the pharmaceutical composition is about 4% or less over about 36 months at about 2-8° C. In another embodiment, the increase in the AV of margetuximab in the pharmaceutical composition is about 3% or less over about 36 months at about 2-8° C.

III. Containers and Kits

The invention also provides containers comprising a pharmaceutical composition (i.e., a margetuximab composition). The invention further provides pharmaceutical packs or kits comprising one or more containers containing a pharmaceutical composition (i.e., a margetuximab composition). In one embodiment, a such container is a vial (e.g., a single-dose vial). In one embodiment, such pharmaceutical pack or kit contains a vial (e.g., single-dose vial). In another embodiment, such container (e.g., vials) contains about 5 mL to about 20 mL of a pharmaceutical composition of the invention. In another embodiment, such pharmaceutical pack or kit contains four vials. In another embodiment, such vials contain about 10 mL of a pharmaceutical composition comprising about 250 mg of margetuximab such that the concentration of margetuximab is about 25 mg/mL per vial. Additionally, one or more other prophylactic or therapeutic agents, for example in a prophylactically effective amount or a therapeutically effective amount, useful for the treatment of a disease can also be included in the pharmaceutical pack or kit. Optionally associated with such container(s) can be a notice in the form prescribed by a governmental agency regulating the manufacture, use or sale of pharmaceuticals or biological products, which notice reflects approval by the agency of manufacture, use or sale for human administration. Optionally associated with such container(s) is a product label describing the indication(s) and instructions for preparation and administration of a dosing solution comprising the margetuximab composition.

The present invention provides kits that comprise a pharmaceutical composition (i.e., a margetuximab composition) that can be used in the above methods. In such kits, the pharmaceutical composition (i.e., a margetuximab composition) is generally packaged in hermetically sealed containers, such as ampoules, vials, sachets, etc. that typically indicate the quantity of the components contained therein. The container may be formed of any pharmaceutically acceptable material, such as glass, resin, plastic, etc. In one embodiment, the container is borosilicate glass vial. In another embodiment, the container is a 5 mL (5 cc), 10 mL (10 cc), or 20 mL (20 cc) vial. In another embodiment, the container is single-dose 10 mL (10 cc) USP Type I borosilicate glass vial. In one embodiment, the container is aseptically filled. In one embodiment, the pharmaceutical compositions (i.e., margetuximab compositions) of such kits are supplied as a liquid solutions. Such liquid solutions are typically to be stored at between 2° C. and 8° C. in the original containers until ready to be administered. However, such solutions may be stored at room temperature (~25° C.) for short periods of time. In one embodiment, such pharmaceutical compositions have a shelf-life of at least about 18 months at 2-8° C. In one embodiment, such pharmaceutical compositions have a shelf-life of about 36 months at 2-8° C. In other embodiments, such pharmaceutical compositions have a shelf-life of at least about 3 months at 25° C. The kit can further comprise one or more other prophylactic and/or therapeutic agents, for example in a prophylactically effective amount or a therapeutically effective amount, useful for the treatment of cancer, in one or more containers; and/or the kit can further comprise one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

The invention particularly contemplates a kit that comprises:
a) a container comprising a pharmaceutical composition, the composition comprising about 21.25 mg/mL to about 28.75 mg/mL of margetuximab, about 0.94 mg/mL to about 1.27 mg/mL of sodium phosphate monohydrate, about 0.49 mg/mL to about 0.67 mg/mL of sodium phosphate dibasic heptahydrate, about 2.47 mg/mL to about 3.34 mg/mL of sodium chloride, about 9.35 mg/mL to about 12.75 mg/mL of L-arginine hydrochloride, about 25.5 mg/mL to about 34.5 mg/mL of sucrose and about 0.05 mg/mL to about 0.20 mg/mL of PS80, and water, wherein the composition has a pH of about 5.8 to about 6.4; and
b) optionally, instructions for administration of the pharmaceutical composition to a subject in need thereof.

In one embodiment, such container will comprise 25 mg/mL±2.5 mg/mL of margetuximab, about 1.08 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, and about 0.1 mg/mL PS80, and water, wherein the composition has a pH of 6.1±0.3.

In one embodiment, such container will comprise 25 mg/mL±2.5 mg/mL of margetuximab, about 1.08 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, and about 0.1 mg/mL PS80, and water, wherein the composition has a pH of 5.8 to 6.4.

In one embodiment, such container will comprise 25 mg/mL±2.5 mg/mL of margetuximab, about 1.1 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, and about 0.1 mg/mL PS80, and water, wherein the composition has a pH of 6.1±0.3.

In one embodiment, such container will comprise 25 mg/mL±2.5 mg/mL of margetuximab, about 1.1 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, and about 0.1 mg/mL PS80, and water, wherein the composition has a pH of 5.8 to 6.4.

The invention particularly contemplates a kit that comprises:
a) a container comprising a pharmaceutical composition, the composition comprising about 21.25 mg/mL to about 28.75 mg/mL of margetuximab, about 0.94 mg/mL to about 1.27 mg/mL of sodium phosphate monohydrate, about 0.22 mg/mL to about 0.30 mg/mL of sodium phosphate dibasic anhydrous, about 2.47 mg/mL to about 3.34 mg/mL of sodium chloride, about 9.35 mg/mL to about 12.75 mg/mL of L-arginine hydrochloride, about 25.5 mg/mL to about 34.5 mg/mL of sucrose and about 0.05 mg/mL to about 0.20 mg/mL of PS80, and water, wherein the composition has a pH of about 5.8 to about 6.4; and b) optionally, instructions for administration of the pharmaceutical composition to a subject in need thereof.

In one embodiment, such container will comprise 25 mg/mL±2.5 mg/mL of margetuximab, about 1.08 mg/mL sodium phosphate monohydrate, about 0.26 mg/mL of sodium phosphate dibasic anhydrous, about 2.9 mg/mL sodium chloride, about 11 mg/mL L-arginine hydrochloride, about 30 mg/mL sucrose, and about 0.1 mg/mL PS80, and water, wherein the composition has a pH of 6.1±0.3.

In one embodiment, such container will comprise 25 mg/mL±2.5 mg/mL of margetuximab, about 1.08 mg/mL sodium phosphate monohydrate, about 0.26 mg/mL of sodium phosphate dibasic anhydrous, about 2.9 mg/mL sodium chloride, about 11 mg/mL L-arginine hydrochloride, about 30 mg/mL sucrose, and about 0.1 mg/mL PS80, and water, wherein the composition has a pH of 5.8 to 6.4.

In one embodiment, such container will comprise 25 mg/mL±2.5 mg/mL of margetuximab, about 1.1 mg/mL sodium phosphate monohydrate, about 0.26 mg/mL of sodium phosphate dibasic anhydrous, about 2.9 mg/mL sodium chloride, about 11 mg/mL L-arginine hydrochloride, about 30 mg/mL sucrose, and about 0.1 mg/mL PS80, and water, wherein the composition has a pH of 6.1±0.3.

In one embodiment, such container will comprise 25 mg/mL±2.5 mg/mL of margetuximab, about 1.1 mg/mL sodium phosphate monohydrate, about 0.26 mg/mL of sodium phosphate dibasic anhydrous, about 2.9 mg/mL sodium chloride, about 11 mg/mL L-arginine hydrochloride, about 30 mg/mL sucrose, and about 0.1 mg/mL PS80, and water, wherein the composition has a pH of 5.8 to 6.4.

As provided above, it is specifically contemplated that the water in such compositions, containers, sealed packages, and kits is sterile, nonpyrogenic, distilled water, and can be Water for Injection, USP, or the equivalent.

In one embodiment, pharmaceutical kits of the invention will include instructional material. The included instructional material of the pharmaceutical kits of the invention or the sealed packages of the invention may instruct that the provided pharmaceutical composition is to be administered for the treatment of cancer, for example in a prophylactically effective amount or a therapeutically effective amount. In one embodiment, the included instructional material of the pharmaceutical kits of the invention or the sealed packages of the invention may instruct that the provided pharmaceutical composition is to be administered in combination with an additional agent which may be provided in the same pharmaceutical kit or in a separate pharmaceutical kit. Such instructional material may instruct that the provided pharmaceutical composition is to be administered once about every 2 weeks, once about every 3 weeks, or more or less often. Such instructional material may instruct that a provided container of pharmaceutical composition comprises about 25 mg/mL (e.g., 250 mg/10 mL) of margetuximab. Such instructional material may instruct that the provided pharmaceutical composition is to be administered at a dose of about 15 mg/kg. Such instructional material may instruct that the provided pharmaceutical composition is to be diluted (e.g., in saline) prior to administration. The included instructional material of the pharmaceutical kits of the invention may combine any set of such information (e.g., it may instruction that a margetuximab-containing pharmaceutical composition is to be diluted in saline and administered at a dose of about 15 mg/kg, and that such dose is to be administered once about every 3 weeks; etc.). Such instructional material may instruct regarding the mode of administration of the included pharmaceutical composition, for example that it is to be administered by intravenous (IV) infusion. The included instructional material of the pharmaceutical kits of the invention may instruct regarding the duration or timing of such administration, for example that the included pharmaceutical composition is composition is to be administered by intravenous (IV) infusion over about 30-240 minutes, or over about 30-120 minutes, etc.

In one embodiment, the instructional material of the pharmaceutical kits of the invention instructs that the pharmaceutical composition in 0.9% sodium chloride is diluted to obtain a dosing solution.

In one embodiment, the instructional material of the pharmaceutical kits of the invention provides a method of administering a pharmaceutical composition of the invention to a subject in need thereof, wherein in the method comprises:

a. diluting the pharmaceutical composition in a container in 0.9% sodium chloride to obtain a dosing solution;
b. inverting the container to mix the diluted solution; and
c. attaching the container containing the dosing solution to a device for administration to the subject.

In one embodiment, the instructional material of the sealed packages of the invention provides a method of administering a pharmaceutical composition of the invention to a subject in need thereof, wherein in the method comprises:

a. diluting the pharmaceutical composition in a container in 0.9% sodium chloride to obtain a dosing solution;
b. inverting the container to mix the diluted solution; and
c. attaching the container containing the dosing solution to a device for administration to the subject.

In one embodiment, the container is an IV bag containing 0.9% sodium chloride.

In one embodiment, the administration of the dosing solution is by intravenous (IV) infusion over about 30 minutes, a period of about 60 minutes, or a period of about 120 minutes.

In one embodiment, the pharmaceutical composition is diluted to obtain a treatment dosage of about 15 mg/kg of margetuximab in the dosing solution.

The included instructional material of the pharmaceutical kits of the invention or the sealed packages of the invention may instruct regarding the appropriate or desired use of the included pharmaceutical composition, for example instructing that such pharmaceutical composition is to be administered for the treatment of cancer, and in certain aspects, a HER2/neu-positive cancer (i.e., a cancer that expresses HER2), for example in a prophylactically effective amount or a therapeutically effective amount. In one embodiment, such cancer is selected from the group consisting of: an adrenal gland cancer, anal cancer, AIDS-associated cancer, alveolar soft part sarcoma, bile duct cancer, a cholangiocarcinoma bile duct cancer, bladder cancer, bone cancer, brain and spinal cord cancer, breast cancer, metastatic breast cancer, carotid body tumor, cervical cancer, an HPV-related cervical cancer, chondrosarcoma, chordoma, chromophobe renal cell carcinoma, clear cell carcinoma, colon cancer, colorectal cancer, desmoplastic small round cell tumor, ependymoma, endometrial cancer, Ewing's sarcoma, extraskeletal myxoid chondrosarcoma, fibrogenesis imperfecta ossium, fibrous dysplasia of the bone, gallbladder or bile duct cancer, gastric cancer, gastroesophageal junction (GEJ), gestational trophoblastic disease, germ cell tumor, head and neck cancer, islet cell tumor, Kaposi's Sarcoma, kidney cancer, leukemia, liposarcoma/malignant lipomatous tumor, liver cancer, a hepatocellular carcinoma liver cancer (HCC), lymphoma, a non-Hodgkin's lymphoma (NHL), lung cancer, small cell lung cancer (SCLC), non-small cell lung cancer (NSCLC), medulloblastoma, melanoma, meningioma, Merkel cell carcinoma, multiple endocrine neoplasia, multiple myeloma, myelodysplastic syndrome, neuroblastoma, neuroendocrine tumors, ovarian cancer, pancreatic cancer, papillary thyroid carcinoma, parathyroid tumor, pediatric cancer, peripheral nerve sheath tumor, pheochromocytoma, pituitary tumor, prostate cancer, posterious uveal melanoma, renal metastatic cancer, rhabdoid tumor, rhabdomyosarcoma, sarcoma, skin cancer, soft-tissue sarcoma, squamous cell cancer, a squamous cell carcinoma head and neck cancer (SCCHN), stomach cancer, synovial sarcoma, testicular cancer, thymic carcinoma, thymoma, thyroid cancer, and uterine cancer.

The included instructional material of the pharmaceutical kits of the invention or the sealed packages of the invention may instruct that such pharmaceutical composition is to be administered for a cancer selected from the group consisting of: breast cancer, metastatic breast cancer, cervical cancer, colorectal cancer, endometrial cancer, gastric cancer, GEJ cancer, or ovarian cancer.

In one embodiment, the included instructional material of the pharmaceutical kits of the invention or the sealed packages of the invention instructs that such pharmaceutical composition is to be administered for treatment of HER2$^+$ breast cancer, or HER2$^+$ metastatic breast cancer. In another embodiment, the included instructional material of the pharmaceutical kits of the invention or the sealed packages of the invention instructs that such pharmaceutical composition is to be administered for treatment of HER2$^+$ cervical cancer. In another embodiment, the included instructional material of the pharmaceutical kits of the invention or the sealed packages of the invention instructs that such pharmaceutical composition is to be administered for treatment of HER2$^+$ colorectal cancer. In another embodiment, the included instructional material of the pharmaceutical kits of the invention or the sealed packages of the invention instructs that such pharmaceutical composition is to be administered for treatment of HER2$^+$ endometrial cancer. In another embodiment, the included instructional material of the pharmaceutical kits of the invention or the sealed packages of the invention instructs that such pharmaceutical composition is to be administered for treatment of HER2$^+$ gastric cancer or HER2$^+$ GEJ cancer. In another embodiment, the included instructional material of the pharmaceutical kits of the invention or the sealed packages of the invention instructs that such pharmaceutical composition is to be administered for treatment of HER2$^+$ ovarian cancer.

In any of the above embodiments, the included instructional material of the pharmaceutical kits of the invention or the sealed packages of the invention may instruct that the pharmaceutical composition is to be administered for treatment of such cancer wherein such cancer is a metastatic cancer. In some embodiments, the included instructional material of the pharmaceutical kits of the invention or the sealed packages of the invention may instruct that the pharmaceutical composition is to be administered for treatment of such cancer wherein such cancer is a primary cancer.

The included instructional material of the pharmaceutical kits of the invention or the sealed packages of the invention may instruct that the pharmaceutical composition is to be administered for treatment of such cancer before, during, or after another treatment for such cancer. In certain of such embodiments, such instructional material may instruction that the pharmaceutical composition is to be administered as a neoadjuvant therapy for treatment of such cancer. In other of such embodiments such instructional material may instruction that the pharmaceutical composition is to be administered as an adjuvant therapy for treatment of such cancer. In other of such embodiments such instructional material may instruction that the pharmaceutical composition is to be administered as a component of a combination therapy for treatment of such cancer.

The included instructional material of the pharmaceutical kits of the invention or the sealed packages of the invention may instruct pharmaceutical composition is to be administered for treatment of such cancer expressing HER2 (i.e., a HER2$^+$ cancer). The instructional material may further specify a particular assay or expression measurement, for example expression of HER2 by immunohistochemistry or fluorescent in situ hybridization. The instructional material may further specify that such HER2 expression is determined by a test approved for use by a regulatory agency (e.g., FDA-approved). Examples of such tests includes, HERCEPTEST™, PATHWAY®, PHARMDX™ and others (see, e.g., those described in, Perez, E. A., et al. (2014) "*HER2 testing: Current Status and Future Directions*," Cancer Treatment Reviews, 40:276-284).

IV. Methods of Administration

The pharmaceutical compositions (i.e., margetuximab compositions) of the present invention may be provided for the treatment, prophylaxis, and amelioration of one or more symptoms associated with a disease, disorder or infection by administering to a subject a therapeutically effective amount or prophylactically effective amount of margetuximab. In one embodiment, such pharmaceutical compositions are substantially purified (i.e., substantially free from substances that limit its effect or produce undesired side effects). In a specific embodiment, the subject is an animal, including a mammal such as non-primate (e.g., bovine, equine, feline, canine, rodent, etc.) or a primate (e.g., monkey such as, a cynomolgus monkey, human, etc.). In one embodiment, the subject is a human. The terms "subject" and "patient" are used herein interchangeably.

As used herein, "a therapeutically effective amount" of margetuximab in a pharmaceutical composition of the invention when used for the treatment of a cancer is an amount which can slow the progression of the cancer; reduce the number of cancer cells in fluids (e.g., blood, peripheral cells or lymphatic fluids), tissue or organs (cytotoxic); allow the number of cancer cells to remain relatively constant (cytostatic); reduce tumor size, inhibit metastasis, inhibit tumor growth and/or ameliorate one or more of the symptoms of the cancer. Therapeutically effective amounts of margetuximab for use in formulating the pharmaceutical compositions of the disclosure are provide herein and/or can be determined, for example, by a health care professional taking into account certain factors such as the type of cancer treated, the route of delivery, the age, weight, severity of the subject's symptoms and response pattern of the subject. As used herein, a "prophylactically effective amount" of margetuximab in a pharmaceutical composition of the disclosure when used for the prophylaxis of a cancer is an amount which can prevent or reduce the risk of occurrence or recurrence of the cancer. As used herein, treatment of a cancer with the pharmaceutical compositions, containers, sealed packages, kits or methods of the disclosure, for example, can comprise or can comprise administering a therapeutically effective amount or prophylactically effective amount of margetuximab to subject in need thereof.

Methods of administering a pharmaceutical composition (i.e., a margetuximab composition) of the invention include, but are not limited to, parenteral administration (e.g., intravenous). In a specific embodiment, the pharmaceutical composition (i.e., a margetuximab composition) of the invention is administered intravenously. The pharmaceutical compositions of the invention may be administered together with other biologically active agents, such as chemotherapeutic agents, including but not limited to capecitabine, eribulin, gemcitabine and vinorelbine.

In one embodiment, the amount of the pharmaceutical composition (i.e., a margetuximab composition) of the invention is determined using a weight-base dose of margetuximab to provide the subject with a therapeutically effective amount or a prophylactically effective amount of margetuximab. The term "weight-based dose" as used herein, refers to a discrete amount of a molecule of the invention to be administered per a unit of patient weight, for example milligrams of drug per kilograms of a subject's body weight (mg/kg body weight, abbreviated herein as "mg/kg"). The calculated dose will be administered based on the subject's body weight at baseline. Typically, a significant (≥10%) change in body weight from baseline or established plateau weight will prompt recalculation of dose. Single or multiple dosages may be given.

Margetuximab can be administered as a weight-based dose (e.g., a mg/kg patient weight dose). Generally, doses of margetuximab (and optionally a further agent) can be used in order to provide a subject with the agent in bioavailable quantities. As used herein, the term "dose" refers to a specified amount of medication taken at one time. The term "dosage" refers to the administering of a specific amount, number, and frequency of doses over a specified period of time; the term dosage thus includes chronological features, such as duration and periodicity.

In certain embodiments, margetuximab is administered to a subject in need thereof at a weight-based dose of from about 6 mg/kg to about 18 mg/kg. In certain embodiments, margetuximab is administered to a subject in need thereof at a dose of about 6 mg/kg, about 8 mg/kg, about 10 mg/kg, about 15 mg/kg, or about 18 mg/kg. In one embodiment, margetuximab is administered to a subject in need thereof at a dose of about 15 mg/kg. With respect to weight-based doses, the term "about" is intended to denote a range that is ±10% of a recited dose, such that for example, a dose of about 15 mg/kg will be between 13.6 mg/kg and 16.5 mg/kg.

A dosage of the pharmaceutical compositions of the invention (i.e., a dose of a margetuximab composition) can be administered at periodic intervals over a period of time sufficient to encompass at least 2 doses, at least 4 doses, at least 6 doses, at least 12 doses, or at least 24 doses (a course of treatment). For example, a dosage may be administered e.g., once every two weeks ("Q2W"), once every three weeks ("Q3W"), once every four weeks ("Q4W"), etc. Such periodic administration may continue for a period of time e.g., for between about 1 to 52 weeks, or for more than 52 weeks. Such course of treatment may be divided into increments, each referred to herein as a "cycle," of e.g., between 2 to 8 weeks, during which a set number of doses are administered. The dose and/or the frequency of administration may be the same or different during each cycle. Factors that may influence the dosage and timing required to effectively treat a subject, include, e.g., the severity of the disease or disorder, formulation, route of delivery, previous treatments, the general health and/or age of the subject, and the presence of other diseases in the subject. Moreover, treatment of a subject with a therapeutically effective amount of a compound can include a single treatment or can include a series of treatments.

A "dosing regimen" is a dosage administration in which a patient is administered a predetermined dose (or set of such predetermined doses) at a predetermined frequency (or set of such frequencies) for a predetermined periodicity (or periodicities). One dosing regimen of the invention comprises administration of a margetuximab composition of the invention at a dose of about 15 mg/kg, administered once every 3 weeks.

It is specifically contemplated that in the above embodiments, administration of the pharmaceutical composition occurs at the predetermined frequency or periodicity, or within about 1-3 days of such scheduled interval, such that administration occurs 1-3 day before, 1-3 days after, or on the day of a scheduled dose, e.g., once every 3 weeks (±3 days). In the above embodiments, the margetuximab composition is administered by intravenous (IV) infusion. In certain embodiments, the pharmaceutical compositions of the invention are administered by IV infusion which can be continuous IV infusion, or discontinuous IV infusion. In certain embodiments, the margetuximab composition is administered by IV infusion according to any of the above dosing regimens for a duration (i.e., course of treatment) of at least 1 month or more, at least 3 months or more, at least 4 months, at least 6 months or more, or at least 12 months or more. A treatment duration of at least 6 months or more, or for at least 12 months or more, or until remission of disease or unmanageable toxicity is observed, is contemplated. In certain embodiments, treatment continues for a period of time after remission of disease. In certain embodiments, treatment may be paused due to illness, adverse event, etc., and is resumed upon resolution, reduction or amelioration of such illness, adverse event, etc.

In certain embodiments of the methods of the invention, the pharmaceutical composition (i.e., the margetuximab composition) is diluted into an IV infusion bag comprising a suitable diluent, e.g., 0.9% sodium chloride (saline) for administration by IV infusion. Since infusion or allergic reactions may occur, premedication for the prevention of such infusion reactions may be utilized and precautions for anaphylaxis should be observed during the antibody administration. In one embodiment, the IV infusion is administered to the subject over about 30 minutes to about 240 minutes. In certain embodiments, the IV infusion is delivered over about 30-120 minutes, about 30-180 minutes, about 30-120 minutes, or about 30-90 minutes, or about 60-90 minutes.

Although, as discussed above, various dosing and administration routes may be employed in order to provide a pharmaceutical composition comprising margetuximab to recipient subjects in need thereof in accordance with the present invention, certain dosing and administrative routes are particularly contemplated for use in such treatment. The pharmaceutical compositions of the invention are particularly useful for the administration of margetuximab (e.g., 15 mg/kg) by IV infusion over about 30 minutes, or over about 60 minutes or over about 120 minutes. Such embodiments are provided in further detail below.

V. Administration of Dosing Solutions Comprising a Pharmaceutical Composition A dosing solution that comprises a pharmaceutical composition (such as the margetuximab composition) is particularly suitable for intravenous administration by gravity or using a stationary infusion pump. The margetuximab composition is combined with 0.9% sodium chloride to obtain a margetuximab dosing solution. In certain embodiments, the administration of the therapeutic dosage will be over at least 30 minutes or at least 120 minutes.

In specific embodiments, a dose of about 15 mg/kg will be administered to the patient or subject. In other specific embodiments, a dose of about 15 mg/kg is administered every three weeks (Q3W). In another specific embodiment, the administration of such doses will be over at least about 30 minutes, over at least about 60 minutes, or over at least about 120 minutes. In another specific embodiment, the administration of the margetuximab dosing solution will be by IV infusion for at least about 120 minutes for an initial dose. In another specific embodiment, the administration of the margetuximab dosing solution will be by IV infusion for at least about 30 minutes Q3W for subsequent doses.

To form a dosing solution, the pharmaceutical composition (i.e., the margetuximab composition) may be added to a container, such as an IV bag, containing 0.9% sodium chloride (nominal volume 100 mL or 250 mL). In one embodiment, the pharmaceutical compositions is swirled gently prior to being added to a container containing 0.9% sodium chloride. In one embodiment, an appropriate volume of the pharmaceutical composition is added to a container containing 0.9% sodium chloride to administer a dose of 15 mg/kg of margetuximab. For example, a final concentration of margetuximab in 250 mL of dosing solution should be between 2.4 to 7.2 mg/mL based on patient body weight in the range of 40 kg to 120 kg. In one embodiment, the container is an IV bag. In a specific embodiment, the IV bag is a polyvinyl chloride (PVC) bag or PVC IV bag with polyamide coating or non-PVC polyolefin or olefin copolymer coating. In one embodiment, an in-line filter is used during administration. In a specific embodiment, a 0.2 µm pore size line-line filter is used. In another specific embodiment, a low protein binding 0.2 µm pore size polyethersulfone (PES) filter is used. The appropriate volume of the pharmaceutical composition should be added to the IV bag and may be gently inverted to mix the dosing solution.

In one embodiment, the prepared dosing solution is used immediately. In another embodiment, the prepared dosing solution is stored at 25° C. or at 2-8° C. for up to 24 hours.

VI. Uses of the Compositions of the Invention

The pharmaceutical compositions, containers, sealed packages, and kits of the invention are useful for the administration of margetuximab to a subject in need thereof. In particular, the pharmaceutical compositions of the invention are useful for the treatment of cancer, and in certain embodiments, for the treatment of a cancer in which HER2/neu is expressed (i.e., a HER2$^+$ cancer), for example in a therapeutically effective amount or a prophylactically effective amount. In some embodiments, such cancer is selected from the group consisting of: an adrenal gland cancer, anal cancer, AIDS-associated cancer, alveolar soft part sarcoma, bile duct cancer, a cholangiocarcinoma bile duct cancer, bladder cancer, bone cancer, brain and spinal cord cancer, breast cancer, metastatic breast cancer, carotid body tumor, cervical cancer, an HPV-related cervical cancer, chondrosarcoma, chordoma, chromophobe renal cell carcinoma, clear cell carcinoma, colon cancer, colorectal cancer, desmoplastic small round cell tumor, ependymoma, endometrial cancer, Ewing's sarcoma, extraskeletal myxoid chondrosarcoma, fibrogenesis imperfecta ossium, fibrous dysplasia of the bone, gallbladder or bile duct cancer, gastric cancer, gastroesophageal junction (GEJ) cancer, gestational trophoblastic disease, germ cell tumor, head and neck cancer, islet cell tumor, Kaposi's Sarcoma, kidney cancer, leukemia, liposarcoma/malignant lipomatous tumor, liver cancer, a hepatocellular carcinoma liver cancer (HCC), lymphoma, a non-Hodgkin's lymphoma (NHL), lung cancer, small cell lung cancer (SCLC), non-small cell lung cancer (NSCLC), medulloblastoma, melanoma, meningioma, Merkel cell carcinoma, multiple endocrine neoplasia, multiple myeloma, myelodysplastic syndrome, neuroblastoma, neuroendocrine tumors, ovarian cancer, pancreatic cancer, papillary thyroid carcinoma, parathyroid tumor, pediatric cancer, peripheral nerve sheath tumor, pheochromocytoma, pituitary tumor, prostate cancer, posterious uveal melanoma, renal metastatic cancer, rhabdoid tumor, rhabdomyosarcoma, sarcoma, skin cancer, soft-tissue sarcoma, squamous cell cancer, a squamous cell carcinoma head and neck cancer (SCCHN), stomach cancer, synovial sarcoma, testicular cancer, thymic carcinoma, thymoma, thyroid cancer, and uterine cancer.

The pharmaceutical compositions, containers, sealed packages, and kits of the invention are particularly useful for the treatment of breast cancer, metastatic breast cancer, cervical cancer, colorectal cancer, endometrial cancer, gastric cancer, GEJ cancer, or ovarian cancer.

In one embodiment, a pharmaceutical composition, container, sealed package, or kit of the invention is used for the treatment of HER2$^+$ breast cancer, or HER2$^+$ metastatic cancer. In one embodiment, a pharmaceutical composition, container, sealed package, or kit of the invention is used for the treatment of HER2$^+$ gastric cancer or HER2$^+$ GEJ cancer. In one embodiment, a pharmaceutical composition, container, sealed package, or kit of the invention is used for the treatment of HER2$^+$ cervical cancer. In one embodiment, a pharmaceutical composition, container, sealed package, or kit of the invention is used for the treatment of HER2$^+$ colorectal cancer. In one embodiment, a pharmaceutical composition, container, sealed package, or kit of the invention is used for the treatment of HER2$^+$ endometrial cancer. In one embodiment, a pharmaceutical composition, container, sealed package, or kit of the invention is used for the treatment of HER2$^+$ ovarian cancer.

VII. Embodiments of the Invention

The invention is directed to the following embodiments E1-E68:

E1 A pharmaceutical composition comprising, about 20 mg/mL to about 100 mg/mL margetuximab, a sodium phosphate monohydrate buffer, a sodium phosphate dibasic heptahydrate buffer, sodium chloride, L-arginine hydrochloride and sucrose as stabilizers, polysorbate 80 ("PS80") and water, wherein the margetuximab is stable.

E2 The pharmaceutical composition of E1, wherein said composition comprises about 0.94 mg/mL to about 1.27 mg/mL of sodium phosphate monohydrate, about 0.49 mg/mL to about 0.67 mg/mL of sodium phosphate dibasic heptahydrate, about 2.47 mg/mL to about 3.34 mg/mL of sodium chloride, about 9.35 mg/mL to about 12.75 mg/mL of L-arginine hydrochloride, about 25.5 mg/mL to about 34.5 mg/mL of sucrose, about 0.05 mg/mL to about 0.20 mg/mL of PS80, and wherein the composition has a pH of about 5.8 to about 6.4.

E3 The pharmaceutical composition of E2, wherein said margetuximab has a concentration of 25 mg/mL±2.5 mg/mL.

E4 The pharmaceutical composition of any one of E1-E3, wherein said sodium phosphate monohydrate has a concentration of about 1.1 mg/mL.

E5 The pharmaceutical composition of any one of E1-E3, wherein said sodium phosphate monohydrate has a concentration of about 1.08 mg/mL.

E6 The pharmaceutical composition of any one of E1-E5, wherein said concentration of sodium phosphate dibasic heptahydrate is about 0.58 mg/mL.

E7 The pharmaceutical composition of any one of E1-E6, wherein said concentration of sodium chloride is about 2.9 mg/mL.

E8 The pharmaceutical composition of any one of E1-E7, wherein said concentration of L-arginine hydrochloride is about 11 mg/mL.

E9 The pharmaceutical composition of any one of E1-E8, wherein said concentration of sucrose is about 30 mg/mL.

E10 The pharmaceutical composition of any one of E1-E9, wherein said concentration of PS80 is about 0.1 mg/mL.

E11 The pharmaceutical composition of any one of E1-E10, wherein said composition has a pH of 6.1±0.3.

E12 The pharmaceutical composition of any one of E1-E11, wherein said composition comprises 25 mg/mL±2.5 mg/mL of margetuximab, about 1.1 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, about 0.1 mg/mL PS80, and wherein the composition has a pH of 6.1±0.3.

E13 The pharmaceutical composition of any one of E1-E12, wherein said composition comprises 25 mg/mL±2.5 mg/mL of margetuximab, about 1.08 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, about 0.1 mg/mL PS80, and wherein the composition has a pH of 6.1±0.3.

E14 The pharmaceutical composition of any one of claims E1-E13, wherein the pharmaceutical composition is a liquid.

E15 The pharmaceutical composition of E14, wherein said about 10 mL volume of said pharmaceutical composition comprises:
a) about 250 mg margetuximab;
b) about 10.8 mg sodium phosphate monohydrate;
c) about 5.8 mg sodium phosphate dibasic heptahydrate;
d) about 29 mg sodium chloride;
e) about 110 mg L-arginine hydrochloride;
f) about 300 mg sucrose;
g) about 1 mg PS80; and
h) water; and wherein said composition has a pH of 6.1±0.3.

E16 The pharmaceutical composition of any one of E1-E15, wherein said margetuximab comprises:
a) the $CDR_L1$, $CDR_L2$ and $CDR_L3$ of the Heavy Chain Variable Domain ($VH_{HER2}$) having the amino acid sequence of SEQ ID NO:1, and
b) the $CDR_H1$, $CDR_H2$ and $CDR_H3$ of the Light Chain Variable Domain ($VL_{HER2}$) having the amino acid sequence of SEQ ID NO:2.

E17 The pharmaceutical composition of any one of E1-E15, wherein said composition has a shelf-life of at least about 18 months at 2-8° C.

E18 The pharmaceutical composition of any one of E1-E15, wherein said composition has a shelf-life of about 36 months at 2-8° C.

E19 The pharmaceutical composition of any one of E1-E18, wherein said composition has an osmolality of about 270-330 mOsm/kg $H_2O$.

E20 The pharmaceutical composition of any one of E1-E19, wherein said composition has an osmolality of about 275-325 mOsm/kg $H_2O$.

E21 The pharmaceutical composition of any one of E1-E20, wherein said composition has an osmolality of about 290-315 mOsm/kg $H_2O$.

E22 The pharmaceutical composition of any one of E1-E21, wherein said composition has an osmolality of about 300 mOsm/kg $H_2O$.

E23 A container comprising the pharmaceutical composition of any one of E1-E22, wherein said container comprises about 10 mL volume of said pharmaceutical composition.

E24 The container of E23, wherein said about 10 mL volume of said pharmaceutical composition is a liquid comprising:
a) about 250 mg margetuximab;
b) about 10.8 mg to about 11 mg sodium phosphate monohydrate;
c) about 5.8 mg sodium phosphate dibasic heptahydrate;
d) about 29 mg sodium chloride;
e) about 110 mg L-arginine hydrochloride;
f) about 300 mg sucrose;
g) about 1 mg PS80; and
h) water; and
wherein said composition has a pH of 6.1±0.3.

E25 A sealed package comprising the pharmaceutical composition of any one of E1-E22 or the container of E23 or E24.

E26 A kit comprising:
a) a container comprising a pharmaceutical composition, said composition comprising about 21.25 mg/mL to about 28.75 mg/mL of margetuximab, about 0.94 mg/mL to about 1.27 mg/mL of sodium phosphate monohydrate, about 0.49 mg/mL to about 0.67 mg/mL of sodium phosphate dibasic heptahydrate, about 2.47 mg/mL to about 3.34 mg/mL of sodium chloride, about 9.35 mg/mL to about 12.75 mg/mL of L-arginine hydrochloride, about 25.5 mg/mL to about 34.5 mg/mL of sucrose and about 0.05 mg/mL to about 0.20 mg/mL of PS80, and water, wherein the composition has a pH of about 5.8 to about 6.4; or
b) a container comprising a pharmaceutical composition, wherein 10 mL of said composition comprises about 250 mg margetuximab, about 10.8 mg sodium phosphate monohydrate, about 5.8 mg sodium phosphate dibasic heptahydrate, about 29 mg sodium chloride, about 110 mg L-arginine hydrochloride, about 300 mg sucrose, about 1 mg PS80, and wherein said composition has a pH of 6.1±0.3; or
c) a container comprising a pharmaceutical composition, wherein 10 mL of said composition comprises about 250 mg margetuximab, about 11 mg sodium phosphate monohydrate, about 5.8 mg sodium phosphate dibasic heptahydrate, about 29 mg sodium chloride, about 110 mg L-arginine hydrochloride, about 300 mg sucrose, about 1 mg PS80, and wherein said composition has a pH of 6.1±0.3; and instructions for administration of the pharmaceutical composition to a subject in need thereof.

E27 The kit of E26, wherein 10 mL of said composition comprises 25 mg/mL±2.5 mg/mL of margetuximab, about 1.1 mg/mL sodium phosphate monohydrate, about 0.58 mg/mL sodium phosphate dibasic heptahydrate, about 2.9 mg/mL sodium chloride, about 11 mg/mL L-arginine hydrochloride, about 30 mg/mL sucrose, about 0.1 mg/mL PS80, and water, and wherein the composition has a pH of 6.1±0.3.

E28 The kit of E26, wherein 10 mL of said composition comprises about 250 mg margetuximab, about 10.8 mg sodium phosphate monohydrate, about 5.8 mg sodium phosphate dibasic heptahydrate, about 29 mg sodium chloride, about 110 mg L-arginine hydrochloride, about 300 mg sucrose, about 1 mg PS80, water, and wherein said composition has a pH of 6.1±0.3.

E29 The kit of any one of E26-E28, wherein said margetuximab comprises:
a) the $CDR_L1$, $CDR_L2$ and $CDR_L3$ of the Heavy Chain Variable Domain ($VH_{HER2}$) having the amino acid sequence of SEQ ID NO:1, and
b) the $CDR_H1$, $CDR_H2$ and $CDR_H3$ of the Light Chain Variable Domain ($VL_{HER2}$) having the amino acid sequence of SEQ ID NO:2.

E30 The pharmaceutical composition of any of E1-E22, the container of any one of E23-E24, the sealed package of E25 or the kit of any one of E26-E29, wherein said water is sterile, nonpyrogenic, distilled water.

E31 A method of treating cancer, comprising administering margetuximab to a subject in need thereof using the pharmaceutical composition according to any one of E1-E22, or E30, the container of any one of E23-E24, or E30, the sealed package of E25 or E30, or the kit of any one of E26-E30.

E32 The method of E66, wherein the container is an IV bag containing 0.9% sodium chloride.

E33 The method of any one of E31-E32, or E66, wherein said dosing solution maintains monomeric purity of said margetuximab for about 24 hours at 25° C. or for about 24 hours at 2-8° C.

E34 The method of any one of E31-E33, or E66, wherein said administration is by intravenous (IV) infusion for at least 30 minutes.

E35 The method of any one of E31-E34, or E66, wherein said administration is by IV infusion for at least 60 minutes E36 The method of any one of E31-E34, or E66, wherein said administration is by IV infusion for at least 120 minutes.

E37 The method of any one of E31-E36, or E66, wherein the pharmaceutical composition is diluted to obtain a treatment dosage of 15 mg/kg of margetuximab.

E38 The method of any one of E31-E37, or E66, wherein an initial administration of the dosing solution is administered as an IV infusion over about 120 minutes.

E39 The method of any one of E31-E38, or E66, wherein subsequent administrations of the dosing solution are administered as an IV infusion over about 60 minutes every 3 weeks.

E40 The method of any one of E31-E38, or E66, wherein subsequent administrations of the dosing solution are administered as an IV infusion over about 30 minutes every 3 weeks.

E41 The method of any one of E31-E40, or E66, wherein said cancer is a HER2/neu-positive (HER2$^+$) cancer.

E42 The method of any one of E31-E41, or E66, wherein said cancer is selected from the group consisting of: an adrenal gland cancer, anal cancer, AIDS-associated cancer, alveolar soft part sarcoma, bile duct cancer, a cholangiocarcinoma bile duct cancer, bladder cancer, bone cancer, brain and spinal cord cancer, breast cancer, metastatic breast cancer, carotid body tumor, cervical cancer, an HPV-related cervical cancer, chondrosarcoma, chordoma, chromophobe renal cell carcinoma, clear cell carcinoma, colon cancer, colorectal cancer, desmoplastic small round cell tumor, ependymoma, endometrial cancer, Ewing's sarcoma, extraskeletal myxoid chondrosarcoma, fibrogenesis imperfecta ossium, fibrous dysplasia of the bone, gallbladder or bile duct cancer, gastric cancer, gastroesophageal junction (GEJ) cancer, gestational trophoblastic disease, germ cell tumor, head and neck cancer, islet cell tumor, Kaposi's Sarcoma, kidney cancer, leukemia, liposarcoma/malignant lipomatous tumor, liver cancer, a hepatocellular carcinoma liver cancer (HCC), lymphoma, a non-Hodgkin's lymphoma (NHL), lung cancer, small cell lung cancer (SCLC), non-small cell lung cancer (NSCLC), medulloblastoma, melanoma, meningioma, Merkel cell carcinoma, multiple endocrine neoplasia, multiple myeloma, myelodysplastic syndrome, neuroblastoma, neuroendocrine tumors, ovarian cancer, pancreatic cancer, papillary thyroid carcinoma, parathyroid tumor, pediatric cancer, peripheral nerve sheath tumor, pheochromocytoma, pituitary tumor, prostate cancer, posterious uveal melanoma, renal metastatic cancer, rhabdoid tumor, rhabdomyosarcoma, sarcoma, skin cancer, soft-tissue sarcoma, squamous cell cancer, a squamous cell carcinoma head and neck cancer (SCCHN), stomach cancer, synovial sarcoma, testicular cancer, thymic carcinoma, thymoma, thyroid cancer, and uterine cancer.

E43 The method of any one of E41-E42, or E66, wherein said cancer is gastric cancer, or GEJ cancer.

E44 The method of any one of E31-E42, or E66, wherein said cancer is breast cancer or metastatic breast cancer.

E45 Use of the pharmaceutical composition according to any one of E1-E22, or E30, the container of any one of E23-E24, or E30, the sealed package of E25 or E30, or the kit of any one of E26-E30, for the treatment of cancer in a subject in need thereof E46 The use of E67, wherein the container is an IV bag containing 0.9% sodium chloride.

E47 The use of any one of E45-E46, or E67, wherein said administration is by IV infusion for at least 30 minutes.

E48 The use of any one of E45-E46, or E67, wherein said administration is by IV infusion for at least 60 minutes.

E49 The use of any one of E45-E46, or E67, wherein the administration of said pharmaceutical composition is by IV infusion for at least 120 minutes.

E50 The use of any one of E45-E49, or E67, wherein the pharmaceutical composition is diluted to obtain a treatment dosage of 15 mg/kg of margetuximab.

E51 The use of any one of E45-E50, or E67, wherein the initial administration of the dosing solution is administered as an IV infusion over about 120 minutes.

E52 The use of any one of E45-E51, or E67, wherein subsequent administrations of the dosing solution are administered as an IV infusion over about 60 minutes every 3 weeks.

E53 The use of any one of E45-E51, or E67, wherein subsequent administrations of the dosing solution are administered as an IV infusion over about 30 minutes every 3 weeks.

E54 The use of any one of E45-E53, or E67, wherein said cancer is a HER2/neu-positive (HER2$^+$) cancer.

E55 The use of any one of E45-E54, or E67, wherein said cancer is selected from the group consisting of: an adrenal gland cancer, anal cancer, AIDS-associated cancer, alveolar soft part sarcoma, bile duct cancer, a cholangiocarcinoma bile duct cancer, bladder cancer, bone cancer, brain and spinal cord cancer, breast cancer, metastatic breast cancer, carotid body tumor, cervical cancer, an HPV-related cervical cancer, chondrosarcoma, chordoma, chromophobe renal cell carcinoma, clear cell carcinoma, colon cancer, colorectal cancer, desmoplastic small round cell tumor, ependymoma, endometrial cancer, Ewing's sarcoma, extraskeletal myxoid chondrosarcoma, fibrogenesis imperfecta ossium, fibrous dysplasia of the bone, gallbladder or bile duct cancer, gastric cancer, GEJ cancer, gestational trophoblastic disease, germ cell tumor, head and neck cancer, islet cell tumor, Kaposi's Sarcoma, kidney cancer, leukemia, liposarcoma/malignant lipomatous tumor, liver cancer, a hepatocellular carcinoma liver cancer (HCC), lymphoma, a non-Hodgkin's lymphoma (NHL), lung cancer, small cell lung cancer (SCLC), non-small cell lung cancer (NSCLC), medulloblastoma, melanoma, meningioma, Merkel cell carcinoma, multiple endocrine neoplasia, multiple myeloma, myelodysplastic syndrome, neuroblastoma, neuroendocrine tumors, ovarian cancer, pancreatic cancer, papillary thyroid carcinoma, parathyroid tumor, pediatric cancer, peripheral nerve sheath tumor, pheochromocytoma, pituitary tumor, prostate cancer, posterious uveal melanoma, renal metastatic cancer, rhabdoid tumor, rhabdomyosarcoma, sarcoma, skin cancer, soft-tissue sarcoma, squamous cell cancer, a squamous cell carcinoma head and neck cancer (SCCHN), stomach cancer, synovial sarcoma, testicular cancer, thymic carcinoma, thymoma, thyroid cancer, and uterine cancer.

E56 The use of any one of E45-E55, or E67, wherein said cancer is gastric cancer, or GEJ cancer.

E57 The use of any one of E45-E55, or E67, wherein said cancer is breast cancer or metastatic breast cancer.

E58 The method of any one of E31-E44, or E66, or the use of any one of E45-E57, or E67, wherein said subject is a human subject.

E59 The pharmaceutical composition of any one of E1-E22, wherein said composition maintains monomeric purity of said margetuximab for at least about 3 months at about 25° C.

E60 The pharmaceutical composition of any one of E1-E22, wherein said composition maintains monomeric purity of said margetuximab for at least about 18 months at about 2-8° C.

E61 The pharmaceutical composition of any one of E1-E24, wherein said composition maintains the charge heterogeneity profile of said margetuximab for at least about 36 months at about 2-8° C.

E62. The pharmaceutical composition of any of E1-E25, wherein said water is sterile, nonpyrogenic, distilled water.

E63. The pharmaceutical composition of any one of E1-E26, wherein said composition is sterile.

E64 A kit comprising the pharmaceutical composition of any one of E1-E27, the container of any one of E28 or E29, or the sealed package of E30 and optionally further comprising instructions for administration of the pharmaceutical composition to a subject in need thereof.

E65 A sealed package comprising the pharmaceutical composition of any one of E1-E27, or the container of any one of E28 or E29, or the kit of any one of claims E31-E35, and optionally further comprising instructions for administration of the pharmaceutical composition to a subject in need thereof.

E66. The method of E31, wherein said method comprises:
a) diluting the pharmaceutical composition in a container in 0.9% sodium chloride to obtain a dosing solution;
b) inverting the container to mix the diluted solution; and
c) attaching the container containing the dosing solution to a device for administration to the subject.

E67 The use of E45, wherein said use comprises:
a) diluting the pharmaceutical composition in a container in 0.9% sodium chloride to obtain a dosing solution;
b) inverting the container to mix the diluted solution; and
c) attaching the container containing the dosing solution to a device for administration to the subject.

E68 The use of any one of E45, E46, or E67, wherein said dosing solution maintains monomeric purity of said margetuximab for about 24 hours at 25° C. or for about 24 hours at 2-8° C.

EXAMPLES

Having now generally described the invention, the same will be more readily understood through reference to the following examples, which are provided by way of illustration and are not intended to be limiting of the present invention unless specified.

Example 1

Development of a Pharmaceutical Composition Containing Margetuximab

As disclosed above, margetuximab comprises a HER2/neu Binding Domain comprising a Heavy Chain having the amino acid sequence of SEQ ID NO:1 and a Light Chain having the amino acid sequence of SEQ ID NO:2, wherein: the Light Chain comprises a Variable Domain ($VL_{HER2}$) that comprises the $CDR_L1$, $CDR_L2$ and $CDR_L3$ of margetuximab and the Heavy Chain comprises a Variable Domain ($VH_{HER2}$) that comprises the $CDR_H1$, $CDR_H2$ and $CDR_H3$ of margetuximab. A stable pharmaceutical composition comprising margetuximab ("the margetuximab drug product (DP) composition"), was developed as a liquid composition in vials.

1.1. Target Product Profile of Margetuximab DP Composition

The target product profile of the margetuximab DP composition is shown below in Table 1.

TABLE 1

| QTTP of Margetuximab DP Composition | |
|---|---|
| Product Attribute | Target |
| Dosage form | Injection: Sterile aqueous solution, preservative-free |
| Protein content per vial | ≥250 mg |
| Dose | 15 mg/kg |
| Protein Concentration | ≥25 mg/mL |
| Shelf life | ≥18 months when stored refrigerated at 2-8° C. |

TABLE 1-continued

| QTTP of Margetuximab DP Composition | |
|---|---|
| Product Attribute | Target |
| Degradants/impurities | Below safety threshold |
| Aggregates | <5% |

1.2 Development of the Margetuximab DP Composition Study Design and Results

An initial formulation (PBS-T) was made comprising 25 mg/mL of margetuximab, 1.08 mg/mL sodium phosphate monobasic, 0.58 mg/mL sodium phosphate dibasic, 8.7 mg/mL sodium chloride, 0.05 mg/mL Polysorbate 80 ("PS80"), at pH 6.1. The stability of margetuximab, was monitored by SE-HPLC, and showed that the purity percentage dropped 1% after freeze and thaw, and it dropped another 1.3% after storage at 2-8° C. for 9 months. To improve the stability of margetuximab, formulation studies were conducted for this antibody molecule. Sucrose was added in the formulation as a cryo-protectant and to stabilize the protein against physical and chemical degradation during long term solution storage. L-arginine hydrochloride was used to assist protein refolding and to mitigate antibody aggregation: it was also added to stabilize the protein in solution. PS80 was selected for stabilizing the protein against interfacial stresses and for preventing the formation of aggregates and particles.

Various formulations were screened to evaluate the effect of pH and buffer/ionic strength in the range 5.0-6.5. For reference, the pI range of margetuximab from cIEF is 8.1-9.1. The buffer salts used in this study were sodium acetate, sodium citrate and sodium phosphate. An excipient screen was performed at pH 5.0 and pH 6.0 using sucrose, sucrose-L-arginine hydrochloride combinations, and trehalose. The effects of addition of these excipients, with increased PS80 concentration from 0.05 mg/mL to 0.1 mg/mL, were compared with the stability of margetuximab in a PBS-T (PBS with 0.05 mg/mL PS80) formulation.

A formulation (F1) comprising 1.1 mg/mL sodium phosphate monobasic, monohydrate, 0.58 mg/mL sodium phosphate dibasic heptahydrate, anhydrous, 2.9 mg/mL sodium chloride, 11 mg/mL arginine hydrochloride, 30 mg/mL sucrose, and 0.1 mg/mL PS80, at pH 6.1 (the heptahydrate form of dibasic sodium phosphate allows for easier dissolution during diafiltration buffer preparation, but use of 0.26 mg/mL sodium phosphate dibasic anhydrous provides an equivalent formulation) was selected for further study because the SE-HPLC results in Table 2 showed improved margetuximab stability as compared to the PBS-T formulation buffer.

TABLE 2

| | Formulation Screening Study Results | | |
|---|---|---|---|
| DS formulation code | After freeze-thaw (% HMW per month) | Liquid at 2-8° C. (% HMW per month) [a] | Liquid at 25° C. (% HMW per month) [a] |
| PBS-T [a] | 1.0 | 0.2 | ND |
| PBS-2T [b] | 0.3 | 0.4 | 1.0 |
| F1 [b] | −0.3 | 0.2 | 0.5 |
| F1 [b] | 0.2 | 0.0 | 0.4 |

T = 0.05 mg/mL PS80;
2T = 0.1 mg/mL PS80;
ND = not determined.
[a] 9 months liquid storage stability.
[b] 2 months liquid storage stability.

Sodium phosphate buffer combined with the selected excipients in the F1 formulation was found to be a suitable buffer at pH 6.1 from a stability perspective. As described in more detail below this conclusion was confirmed by long-term formulation stability studies of the margetuximab DP composition, manufactured with the components of the F1 formulation, after freeze/thaw of the drug substance. This F1 formulation buffer kept frozen margetuximab DP composition stable at ≤−60° C. The components of the selected margetuximab DP composition are shown in Table 3.

TABLE 3

| Margetuximab DP Composition | |
|---|---|
| DP Composition Components | DP Composition |
| Margetuximab monoclonal antibody | 25 mg/mL in formulation buffer |
| Sodium phosphate dibasic, heptahydrate | 0.58 mg/mL |
| Sodium phosphate monobasic, monohydrate | 1.1 mg/mL* |
| Sodium chloride | 2.9 mg/mL |
| Sucrose | 30 mg/mL |
| L-arginine hydrochloride | 11 mg/mL |
| Polysorbate 80 ("PS80") | 0.10 mg/mL |
| Water for Injection | q.s. to 1 mL |

*Long-term stability studies demonstrated that DP compositions comprising 1.08 mg/mL to 1.1 mg/mL sodium phosphate monobasic, monohydrate are equivalent.

1.3. Long-Term Formulation Stability Studies

Long term physical and chemical stability studies were performed on margetuximab F1 formulation compared to two other formulations. The monomer purity percentage and subvisible particle (SVP) count profiles were comparable in these 3 formulations. However, the potency results after 18 months storage at 2-8° C. indicated that the F1 formulation at pH 6.1 retained higher potency compared to the other two formulations at pH 5.1. These results further confirmed that the F1 formulation at pH 6.1 is an optimized formulation based on stability and potency data at 2-8° C. for 18 months storage. Further, stability studies indicate that the F1 formulation supports storage for 36 months at 2-8° C. Table 4 shows the data from the long-term stability study of the margetuximab F1 formulation.

TABLE 4

Long-term (18 month) Formulation Stability Study

Stability at 2-8° C.

| Margetuximab Formulation | % Monomer Purity by SE-HPLC | | Visual Appearance Subvisible Particle (SVP) Counts by HIAC (counts/mL) | | | % Acidic Variants and Basic Variants by IEF | | Potency [a] |
|---|---|---|---|---|---|---|---|---|
| | t = 0 | t = 18 months | t = 0 [a] | t = 18 months | | t = 0 [a] | t = 18 months | t = 18 months |
| Formulation F1: 10 mM sodium phosphate, 3% w/v sucrose, 50 mM L-Arg · HCl, 50 mM NaCl 0.1 mg/mL PS80, pH 6.1 | 98.0 | 97.5 | SO, L, MPP | SO, L, MPP | ≥10 µm: 121 ≥25 µm: 1 | AV: 30.6 BV: 14.9 | AV: 40.8 BV: 14.8 | 1.08 |
| 10 mM sodium acetate, 3% w/v sucrose, 50 mM L-Arg · HCl, 50 mM NaCl 0.1 mg/mL PS80, pH 5.1 | 98.4 | 97.4 | SO, L, MPP | SO, L, MPP | ≥10 µm: 7 ≥25 µm: 1 | AV: 30.6 BV: 14.9 | AV: 22.9 BV: 28.0 | 0.76 |
| 10 mM sodium acetate, 9% w/v sucrose, 0.1 mg/mL PS80, pH 5.1 | 98.4 | 98.0 | C, L, MPP | C, L, MPP | ≥10 µm: 6 ≥25 µm: 1 | AV: 30.6 BV: 14.9 | AV: 24.5 BV: 26.2 | 0.89 |

SO = slightly opalescent;
C = clear;
L = colorless;
MPP = may contain visible particles when samples are shaken;
AV = acidic variants;
BV = basic variants
[a] At time zero SVP and potency data were not acquired. IEF data at time zero were measured using the margetuximab Reference Standard

1.4. Margetuximab Composition Characterization and Robustness Study Using Design of Experiments A Design of Experiments (DoE) study was then performed to verify the robustness of the margetuximab composition for use and to develop a control strategy for the margetuximab DP composition manufacturing process. The DoE study was used to demonstrate the robustness of the margetuximab DP composition over a range of composition parameters beyond the target composition, the margetuximab DP composition was evaluated at the recommended storage temperature of 2-8° C. for 12 months and at accelerated temperature condition of 25° C. for 6 months.

Ranges of five composition parameters were investigated as shown in Table 5 and Table 6. In addition to all the formulations designed for the DoE study design (F1-F12), center point formulations F13 and F14, and low & high protein concentration formulations, F7 and F15, respectively, were evaluated. F15 had a higher margetuximab concentration of 27.5 mg/mL. Margetuximab concentration in formulation F7 was reduced to 22.5 mg/mL. All other factors in formulations F7 and F15 were identical. The excipient concentration ranges are ±15% of target, and the PS80 concentration range is ±50% of target in the DoE study. DoE study pH was evaluated within the pH 5.8 to pH 6.6 based on limitations due to the buffering capacity of sodium phosphate buffer. The protein concentration range evaluated was target ±10%.

TABLE 5

Target Formulation and DoE Study Ranges Evaluated

| Parameter | Target Value | DoE Study Range |
|---|---|---|
| Protein concentration | 25 mg/mL | 22.5-27.5 mg/mL |
| Combined concentration of phosphate buffer and NaCl | 60 mM | 51-69 mM |
| pH | 6.1 | 5.8-6.6 |
| Sucrose | 3% | 2.55-3.45% |
| L-arginine HCl | 50 mM | 42.5-57.5 mM |
| PS80 | 0.1 mg/mL | 0.05-0.15 mg/mL |

TABLE 6

DoE Study Design for Margetuximab Formulation Robustness Evaluation

| Formulation (F) | Protein conc. (mg/mL) | % Sucrose w/v | L-Arg · HCl mM | Sodium Chloride and Sodium Phosphate mM | pH | % PS80 w/v |
|---|---|---|---|---|---|---|
| 1 | 25 | 3.45 | 57.5 | 69 | 6.6 | 0.015 |
| 2 | 25 | 2.55 | 57.5 | 51 | 6.6 | 0.015 |
| 3 | 25 | 2.55 | 42.5 | 69 | 5.8 | 0.015 |
| 4 | 25 | 3.45 | 42.5 | 51 | 6.6 | 0.005 |
| 5 | 25 | 2.55 | 57.5 | 51 | 5.8 | 0.005 |
| 6 | 25 | 2.55 | 42.5 | 69 | 5.8 | 0.005 |
| 7 | 22.5 | 2.55 | 42.5 | 51 | 6.6 | 0.005 |
| 8 | 25 | 3.45 | 42.5 | 51 | 5.8 | 0.015 |
| 9 | 25 | 3.45 | 57.5 | 51 | 5.8 | 0.005 |

TABLE 6-continued

DoE Study Design for Margetuximab Formulation Robustness Evaluation

| Formulation (F) | Protein conc. (mg/mL) | % Sucrose w/v | L-Arg · HCl mM | Sodium Chloride and Sodium Phosphate mM | pH | % PS80 w/v |
|---|---|---|---|---|---|---|
| 10 | 25 | 3.45 | 57.5 | 69 | 5.8 | 0.005 |
| 11 | 25 | 2.55 | 57.5 | 69 | 6.6 | 0.005 |
| 12 | 25 | 3.45 | 42.5 | 69 | 6.6 | 0.015 |
| 13 | 25 | 3 | 50 | 60 | 6.1 | 0.01 |
| 14 | 25 | 3 | 50 | 60 | 6.1 | 0.01 |
| 15 | 27.5 | 2.55 | 42.5 | 51 | 6.6 | 0.005 |

The pH, concentration and osmolality data of the formulations were analyzed only for the initial T=0 samples and all results were as expected. The effects of buffer, pH and excipients on high molecular weight species (HMWS), acidic variants (AV), basic variants (BV) and subvisible particles (SVP) were monitored by size exclusion chromatography (SE-HPLC), ion exchange chromatography (IE-HPLC) and light obscuration (HIAC), respectively.

The analytic assays and stability matrix used for the DoE formulation robustness study are show below in Table 7 and Table 8.

TABLE 7

Analytical Tests Performed on DOE Stability Study Samples at 2-8° C.

| Test | Time t = 0 | t = 1 month | t = 3 months | t = 6 months | t = 12 months |
|---|---|---|---|---|---|
| Visual Appearance | x | x | x | x | x |
| pH | x | NT | NT | x | x |
| SE-HPLC | x | NT | x | x | x |
| Subvisible Particulates | x | NT | x | x | x |
| IE-HPLC | x | NT | NT | x | x |
| Potency (Cell growth inhibition bioassay) | x | NT | NT | x | x |

NT = not tested

TABLE 8

Analytical Tests Performed on DOE Stability Study Samples at 25° C.

| Test | Time t = 0 | t = 1 month | t = 3 months | t = 6 months |
|---|---|---|---|---|
| Visual Appearance | x | x | x | x |
| SE-HPLC | x | x | x | x |
| Subvisible Particulates | x | x | x | x |
| IE-HPLC | x | x | x | x |
| Potency (Cell growth inhibition bioassay) | x | NT | NT | x |

NT = Not tested 1.5. Results from Formulation Robustness Stability Study Using Design of Experiment The results from the formulation robustness stability study for different product quality attributes are discussed in the sections below. The pH and osmolality measured for all formulation conditions after preparation were at or close to target, and pH did not change across all conditions on stability.

1.5.1. Results of % Monomer, % HMW and % LMW Species Monitored by SE-HPLC

SE-HPLC studies demonstrated that the formulated samples stored at 2-8° C. were stable for 15 months with the data trend showing no major changes in stability. The % HMW (high molecular weight) species content of higher pH 6.6 formulations in the DOE design space was about 0.2% higher than that of lower pH 5.8 formulations. Even after 6-month storage at 25° C., the monomer purity decreased to only ~97-98%. The % HMW species content increased 0.5-0.7% and % LMW (low molecular weight) species increased ~0.4% over 6 months in all formulations, as expected, at this accelerated stability storage condition. The % BMW species content of the higher pH 6.6 formulations were 0.3-0.7% higher than that of lower pH 5.8 formulations stored at 25° C. over 6 months.

These stability data demonstrate that variations in the pH, excipients and buffer conditions of the margetuximab F1 formulation result in no major changes, within the ranges evaluated, in the % monomer, % BMW and % LMW species as a function of storage time at the recommended 2-8° C. storage temperature.

1.5.2. Charge Heterogeneity Changes Monitored by IE-HPLC

The acidic/basic variants and main peak of margetuximab DOE samples were measured by IE-HPLC. The 12-month timepoint stability samples were tested at 13 months by IE-HPLC.

Minor changes were detected by IE-HPLC for margetuximab stored at 2-8° C. for 13 months. Over 13 months, acidic species increased by ~8% for high pH 6.6 formulations, while the species decreased by ~5% for low pH 5.8 formulations at 2-8° C. Basic species increased 2.5-5% for low pH 5.8 formulations, while for pH 6.1 formulations they increased by ~8-9%. No major changes in basic species were observed for the pH 6.6 formulations.

Acidic variants of margetuximab stored at 25° C. for over 6 months increased significantly by ~40% for pH 6.6 formulations, while these variants increased by ~5% for pH 5.8 formulations. At 25° C. basic variants increased ~18% for pH 5.8 formulations, while for pH 6.6 formulations they decreased ~5% over 6 months.

The results of the stability study showed that pH=6.1±0.3 is the optimal pH range where the degradants are the lowest at the recommended 2-8° C. storage. The pH 6.1 formulation condition at 2-8° C. showed an increase in basic species monitored by IE-HPLC with time of storage, while acidic species variants showed a minor increase. However, it was observed that at pH 6.1 at 25° C. storage condition, acidic variants increased more than basic variants.

These formulation robustness stability studies demonstrate that the pH of the excipients and buffer conditions of the margetuximab F1 formulation results in only minor changes in the charge heterogeneity profile, within the ranges evaluated, during storage at the recommended storage temperature of 2-8° C. These minor changes in the charge heterogeneity variants did not translate to major changes in the relative potency of margetuximab as shown in Table 9.

1.5.3. Visual Appearance and Subvisible Particles

Visual appearance results of all the formulation samples stored at 2-8° C. over 12 months were clear, colorless, and contained no visible particles during storage stability.

Subvisible particle (SVP) data were acquired from HIAC light obscuration-based assay on DOE samples stored at 2-8° C. and 25° C. The SVP counts were found to be well within acceptable limits over the range of PS80 concentrations studied. There was no major increase in SVP count over the time course of the study, both in terms of absolute particle counts and relative to the compendia specification: ≤6000 particles/vial for ≥10 μm particles, and ≤600 particles/vial for ≥25 μm particles.

Based on the visual appearance results and subvisible particle data, it was confirmed that PS80 levels evaluated were effective in stabilizing the margetuximab DP composition against particle formation. The summarized HIAC data, measured at different storage conditions, are as follows. For samples stored at 2-8° C. for 13 months, the SVP count for ≥10 μm particles was ≤80 counts/mL, and for ≥25 μm particles, it was ≤30 counts/mL. For samples stored at 25° C. for 6 months, the SVP count for ≥10 μm particles was ≤70 counts/mL, and for ≥25 μm particles, it was ≤30 counts/mL.

1.5.4. Relative Potency Changes Monitored by Cell Growth Inhibition Bioassay

Relative potency of select formulation DoE samples were evaluated using cell growth inhibition bioassay on select samples that showed changes in the charge heterogeneity profile to monitor functional aspects of the antibody. Potency data on selected formulations F2 (pH=6.6), F5 (pH=5.8), and F13 (target pH=6.1) stored at 2-8° C. for 12 months are shown in Table 9. Formulation F2 and F5 were chosen for potency measurements because they bracket the low and high end of the pH range and they contain the same concentrations of the excipients. Margetuximab drug product relative potency is comparable in the selected low and high pH formulations stored at 2-8° C. over 12 months.

TABLE 9

Potency Assay Results of Selected Formulations

| Formulation | pH | % Relative Potency (12 Months) |
|---|---|---|
| F2 | 6.6 | 96 |
| F5 | 5.8 | 87 |
| F13 | 6.1 | 86 |

1.5.5. Results

The excipient concentrations and solution conditions selected for the margetuximab F1 formulation were suitable for drug product stability at the recommended storage temperature of 2-8° C. The stability study results confirm that margetuximab formulation F1 was robust within the DoE formulation ranges tested. The pH of all formulations was at or close to target. The formulation pH, which was varied in the DoE study between pH 5.8-6.6, had no practical impact on margetuximab monomer content at 2-8° C. and no impact on the % HMW and % LMW content by SE-HPLC, subvisible and visible particles. The formulation at pH 6.1 was optimal with respect to charge variants monitored by IE-HPLC as formulations at pH 5.8 shower higher basic variants compared to other pH conditions and formulations at pH 6.6 show higher acidic variants than the other pH conditions. Across this pH range, margetuximab DoE study samples demonstrated acceptable potency for up to 12 months storage at 2-8° C. In addition to the formulation robustness data shown here, the F1 formulation has consistent and acceptable stability for 36 months.

1.6. Formulation Development Summary

The margetuximab DP composition was designed by the addition of excipients selected for cryo-preservation and freeze/thaw protection (sucrose), colloidal stabilization against protein aggregation and conformational stabilization (L-Arginine.HCl) and for stabilization at the air/solution interface (PS80 surfactant). Sodium chloride was chosen as a tonicity agent for the formulation. The choice of composition buffer pH target/range and buffering salt was driven by considerations for conformational stability, colloidal stability and bio-chemical stability.

A design of experiments (DoE) study was performed to verify the robustness of the margetuximab DP composition in vials within ranges of formulation parameters specified for the study.

The effects of pH and excipient concentrations on product quality attributes have been investigated, and it has been shown that manufacturing process tolerance-driven variations in pH and formulation variables have controlled effects on the margetuximab DP composition, which lie well within the bounds of the DP release specifications. The results of Multivariate Analysis (MVA) on DoE study samples stored at 2-8° C. over 12 months confirmed that the margetuximab DP composition is stable in the wide ranges tested for pH, protein concentration, excipient and PS80 concentrations. The statistical MVA model output provided assurance at 95% confidence level that the current margetuximab DP composition can robustly withstand variations in excipient concentration and PS80 concentration.

The model analysis further established the conclusion that while pH had a statistically significant impact on margetuximab monomer and charge variant stability in solution, the DoE study experimental data demonstrated that the effects of pH were not practically significant. Basic charge variants increase at pH 5.8, while acidic charge variants increase at pH 6.6 with increasing storage temperature and time. The lower end of the investigated pH range of 5.8-6.6 was favored for margetuximab stability. Therefore, the target pH 6.1 with ±0.3 tolerance determined from this DoE study was optimal. Moreover, pH is controlled tightly in the margetuximab DP composition to within ±0.3 units. Protein concentration and buffer salt concentration did not impact stability at 2-8° C.

In summary, the DoE study, confirmed the suitability of the buffer to maintain pH and corresponding stability of the margetuximab DP composition. The combined concentration of the buffer salts and the concentration of the sodium chloride excipient were varied within ±15% of the target concentration, to and the results indicated that the buffer strength variances did not have a significant impact on the formulation's overall stability when stored at the DP's recommended storage temperature of 2-8° C.

1.7. How the Margetuximab Composition is Supplied

Margetuximab DP composition is supplied as a sterile buffered aqueous solution and presented in USP and Ph. Eur. conforming Type I borosilicate 10 cc glass vials capped with a 20 mm FluroTec® and B2-40 coated butyl rubber stoppers. The components of the margetuximab DP composition are provided in Table 3. The nominal content of each margetuximab DP composition vial is 10 mL. Each vial is filled with 10.5-10.8 mL of liquid. An overfill is included to ensure sufficient volume for withdrawal of 10 mL (250 mg) of margetuximab for dose delivery. The target fill volume, deliverable volume and vial/syringe hold up volumes were determined by extractable volume testing. Margetuximab DP composition is a colorless, opalescent solution that is essentially free from visible particles. Inherent proteinaceous particles may be present in the margetuximab DP composition vials.

Example 2

Margetuximab IV Administration Compatibility Studies

Margetuximab DP composition is available in a single-dose vial and is administered as an intravenous (IV) infusion following dilution in 0.9% Sodium Chloride Injection, USP (normal saline). The dilution is calculated based upon the patient's body weight and the dose. To prepare the infusion, solution dilution of margetuximab is performed in a commercially available IV administration bag containing normal saline. The infusion solution is administered to the patient from the dose-prepared normal saline IV bag with a commercially available IV pump and IV administration tubing set. As described in more detail below, stability and compatibility studies were performed with the dilution and storage of dose-prepared margetuximab up to 24 hours at 25° C. and IV administration of margetuximab using unfiltered and filtered IV infusion sets for 30-minute, 60-minute and 120-minute IV infusion periods.

In the initial compatibility studies, margetuximab DP composition was diluted in IV bags of the same composition as those commonly used in the clinic, i.e., polyvinyl chloride (PVC), polyolefin, and polyolefin copolymer, which were held at 25° C. The dilution scheme in the test IV bags followed a bracketing approach, whereby multiple drug concentrations were tested for each IV bag type, representing high and low dose concentrations. Structural integrity of margetuximab was maintained under all conditions and time points as assessed by size exclusion chromatography (SE-HPLC) and protein concentration recovery. These studies support the stability of margetuximab and its compatibility for clinical administration when diluted in normal saline in PVC, polyolefin, and polyolefin copolymer IV bags.

2.1. Initial Compatibility Studies with Diluents and Infusion Sets (120 Minute IV Infusion)

Three compatibility studies of margetuximab were conducted using normal saline as a diluent. A fourth compatibility study was performed to implement the filtered extension sets to reduce any subvisible proteinaceous particles. This study was performed to ensure margetuximab DP composition compatibility and stability with an IV infusion set with low protein binding 0.2 µm pore size PES filter.

The dose cohort ranges, the types of IV bags/infusion set studied and key study outcomes are summarized in Table 10.

TABLE 10

Compatibility Studies Conducted

| Dose Range (mg/kg) | IV Bag Material of Construction | IV Infusion Set | Study Outcome |
|---|---|---|---|
| 0.1-15 | PVC | NT | Normal saline-diluted DP is compatible with PVC bag. |
| 3-15 | Polyolefin and copolymer of olefins | NT | Normal saline-diluted DP is compatible with both bag types. |
| 3-15 | PVC | Unfiltered B. Braun IV infusion set | Normal saline-diluted DP is compatible with PVC bag and unfiltered IV infusion set. |
| 3-15 | Polyolefin | B. Braun low binding 0.2 µm pore size PES in-line filter infusion set | Normal saline-diluted DP compatible with Polyolefin bag and filtered infusion set; the in-line filter effectively reduced the subvisible particle counts. |

NT = Not tested

The dilution scheme in the 250 mL IV bags followed a 40-120 kg patient weight bracketing approach using the dosing cohort assigned to each study. The effect of holding times of margetuximab dose solution in various IV bags at ambient temperature (~25° C.) and IV infusion time was assessed using analytical assays shown in Tables 11A-11B.

Test samples removed from the IV bags were analyzed for protein concentration by UV spectroscopy at A280 to detect potential loss of margetuximab due to adsorption and for structural integrity by monitoring % monomer and % High Molecular Weight (HMW) species of margetuximab by SE-HPLC. The summarized analytical results of the compatibility studies using normal saline as a diluent with and without IV infusion extension sets are shown in Tables 11A-11B. The recovery of margetuximab stored for up to 8 hours after dilution in IV bags was ≥82.2% at the lowest concentration tested (0.018 mg/mL), and ≥95.2% at all other concentrations tested (0.090 mg/mL, 0.50 mg/mL, and 7.2 mg/mL). Recovery of margetuximab after passing the infusion solutions through standard IV administration sets was ≥98.2%. Structural integrity of margetuximab was maintained under all conditions and time points. These data supported the stability of margetuximab and its compatibility for clinical administration when diluted in normal saline in PVC, polyolefin, and copolymer of olefins IV bags.

Data shown in Tables 11A-11B confirmed that margetuximab DP composition is compatible in commercially available normal saline IV bags made of PVC and polyolefin. The studies demonstrated the compatibility and stability of margetuximab in normal saline IV bags when administered over 120 minutes using (PES) filtered IV administration sets. The recovery of margetuximab was acceptable and its structural integrity was maintained. No adverse trends were seen with respect to subvisible or visible particle formation and this further supported the recommendation to use filtered IV administration sets in the clinical setting to mitigate the potential risk of particles being administered to patients.

TABLE 11A

Summarized Analytical Data from Early Clinical Development Compatibility Studies (120 Minute Infusion Time)

| Set | Clinical Dosing (mg/kg) | Tested Dose (mg/mL) and Diluent | Bag Material (brand, vendor) and Volume (mL) | Extension Set |
|---|---|---|---|---|
| A | Initial dosing range: 0.1 to 15 mg/kg | 0.02, 0.09, and 7.2 mg/mL; Normal saline diluent | PVC (Viaflex ®; Baxter); 50 mL | NT |
| B | Narrowed range: | 0.5 and 7.2 mg/mL; | Polyolefin (PO) (Green-flex 2 ®; | NT |

TABLE 11A-continued

Summarized Analytical Data from Early Clinical Development Compatibility Studies (120 Minute Infusion Time)

| Set | Clinical Dosing (mg/kg) | Tested Dose (mg/mL) and Diluent | Bag Material (brand, vendor) and Volume (mL) | Extension Set |
|---|---|---|---|---|
|  | 3-15 mg/kg | Normal saline diluent | DaiHan Pharm); Copolymer of olefins[a] (CO; Excel ®; B. Braun); 250 mL |  |
| C | 3-15 mg/kg | 0.02, 0.09 and 7.2 mg/mL; Normal saline diluent | PVC (Viaflex ®; Baxter); 50 mL | Unfiltered infusion set |
| D | 3-15 mg/kg | 0.5 and 9 mg/mL; Normal saline diluent | Polyolefin (Green-flex 2 ®); DaiHan Pharm); 250 mL | 0.2 μm filtered infusion set |

NT = Not tested
[a] Olefins used in B. Braun Excel IV bag are ethylene and propylene.

TABLE 11B

Summarized Analytical Data from Early Clinical Development Compatibility Studies (120 Minute Infusion Time)

| Set | Time at ~25° C., t (hour) | Infusion Time/ Method | Flow-rate (mL/hr) | % Protein Recovery | % Monomer; %HMW (SE-HPLC) |
|---|---|---|---|---|---|
| A | t = 4, 8, 24 | NA | NA | ≥79.6 at 0.02 mg/mL ≥95.7 for 0.09 and 7.2 mg/mL | 98.5-99.2; 0.6-1.2 |
| B | t = 4, 8, 24 | NA | NA | 95.2-101.6 (PO) 99.0-104.2 (CO) | 98.2-98.7; 1.2-1.7 (for PO) 98.6-98.8; 1.0-1.3 (for CO) |
| C | t = 4 | 120-minute IV infusion by gravity | 125 | 98.2-106.6 | 98.1-99.3; 0.6-1.8 |
| D | t = 4 | 120-minute IV infusion with peristatic pump | 125 | 97.9-100.5 | 97.6-98.0; 1.8-2.2 |

NA = Not Applicable

2.2. Final Compatibility Study with Normal Saline and Infusion Components (30- and 60-Minute IV Infusion Times)

This study describes the compatibility of margetuximab DP composition with diluents used for dilution of the margetuximab DP composition for IV administration over about 30 or about 60 minutes. These simulated IV infusion compatibility studies were performed to support a 30- or 60-minute infusion time for administration of margetuximab.

The worst-case scenario for evaluating compatibility with IV infusion bag is the storage time of dose solution in IV bags at the room temperature for low and high protein concentrations, bracketing the range of protein concentration allowed in the bags. The justification is that protein adsorption and related instability can happen over time of exposure at higher temperature (~25° C.) and at low to high protein concentrations. In the case of margetuximab, worst-case scenario that was simulated during studies to support compatibility is storage time of 24 hours prior to infusion at 25° C. for 0.5 to 7.2 mg/mL in 0.9% Sodium Chloride Injection, USP IV bags.

The worst-case scenario for evaluating compatibility with IV tubing used for dose administration is the flow rate of IV infusion. The justification is that different flow rates can cause potential differences of shear force that can affect the physical stability of the molecule. In the case of margetuximab dose administration, only polyethylene (PE)-coated PVC tubing sets with 0.2 μm pore size PES inline filter were used during simulated studies with different bag types for evaluating the effect of flow rates corresponding to 30 to 120 minute of infusion time on product quality.

Compatible diluents and components to be used for IV administration of the margetuximab DP composition, as well as the infusion time and flow rates are summarized in Table 12 below. Combinations of IV bags with respective filter infusion sets are assigned a unique identifying code (i.e., A, B, C, D), for abbreviated description in tables in this section. The 60-minute infusion study evaluated a broad range of component sets A, B, C and D, and the 30-minute infusion study compared component sets A and B. Detailed data that scientifically justify the selection of these components are described in subsequent sections.

TABLE 12

Infusion Components Studied for Commercial Margetuximab DP IV Infusion (30- and 60-Minute Infusion Times)

| Description Code | USP Normal Saline IV Bag Material of Construction, Vendor and Nominal Fill Volume | Filter Infusion Pump Set | Nominal Infusion Time (min) | Nominal Flow rate (mL/hr) |
|---|---|---|---|---|
| Component Set A | Copolymer of olefins[a] B. Braun Excel ®; 250 mL | B. Braun (USA) Vista ® Basic, Low binding, 0.2 μm pore size polyethersulfone (PES) filter | 30 [b]; 60 | 500; 250 |
| Component Set B | Polyvinylchloride (PVC), Baxter Viaflex ®; 250 mL | B. Braun (USA) Vista ® Basic, Low binding, 0.2 μm pore size PES filter | 30 [b]; 60 | 500; 250 |

TABLE 12-continued

Infusion Components Studied for Commercial Margetuximab DP IV Infusion (30- and 60-Minute Infusion Times)

| Description Code | USP Normal Saline IV Bag Material of Construction, Vendor and Nominal Fill Volume | Filter Infusion Pump Set | Nominal Infusion Time (min) | Nominal Flow rate (mL/hr) |
|---|---|---|---|---|
| Component Set C | Polyolefins (polyethylene and polypropylene) and polyamide, Baxter Viaflo ®; 100 mL | B. Braun (USA) Vista ® Basic, Low binding, 0.2 μm pore size PES filter | 60 | 100 |
| Component Set D | Polyolefins (polyethylene and polypropylene) and polyamide, Baxter Viaflo ®; 250 mL | B. Braun (UK) Sterifix ®; Low binding, 0.2 μm pore size PES filter | 60 | 250 |

[a] Olefins used in B. Braun Excel IV bag are ethylene and propylene.
[b] The actual infusion time and flow rate to simulate a 30 min infusion were 20 min and 833 mL/h, respectively.

2.2.1. Experimental Plan and Data Summary

To support shorter administration times the following studies were conducted with 30- and 60-minute simulated infusion using the margetuximab DP composition. The compatibility of margetuximab was evaluated by diluting margetuximab DP composition into normal saline IV bags. The compatibility of the IV extension set materials consisting of polyethylene (PE)-coated PVC tubing sets with PES inline filters was evaluated. A bracketed approach was used to calculate the total dose for a range of patient body weights shown in Table 13. The dilution was calculated based upon the dose of 15 mg/kg and patient body weight.

TABLE 13

Dose Calculation Based on Patient Body Weight Range

| Dose Type | Patient Body Weight (kg) | Dose (mg/kg) | Total Dose (mg) | Dose Concentration (mg/mL) |
|---|---|---|---|---|
| Low Dose | 40 (minimum) | 15 | 600 | 0.5 (low dose concentration) |
| High Dose | 120 (maximum) | 15 | 1800 | 7.2 (high dose concentration) |

In these compatibility studies, the saline-diluted margetuximab samples that were held in IV bags at ambient temperature ~25° C. were collected at initial time (t=0), 8 hours and 24 hours. The study was performed at room temperature as a worst-case temperature and data results also apply for 2-8° C. storage condition considering that the solubility of the DP in saline should be comparable at these temperatures. Samples were collected after 60-minute simulated administration through the in-line filter IV set. Samples were also collected from a 20-minute simulated infusion after passing through the in-line filter IV set to evaluate the flow rate for 30-minute infusion. The collected samples were evaluated by protein concentration and recovery, visual inspection, pH, SE-HPLC, IE-HPLC, HIAC, and potency by cell growth inhibition bio-assay.

All analytical data are comparatively discussed for respective quality attributes in the low and high dose concentration cases for margetuximab DP composition administration. Apparent recovery percentages over 100% reflect assay uncertainty and sample dilution error using syringe. The hold samples were held in an IV bag and not filtered.

2.2.2. Compatibility Study Data: Protein Concentration, Recovery, and pH

Protein concentration, recovery and pH data are presented in Table 14 for 30-minute and 60-minute simulated infusions, and 24 hour hold time at room temperature in the IV bag.

The pH of margetuximab diluted into normal saline is around 6.0, which is close to the margetuximab DP composition pH, in which the margetuximab antibody is most stable. In low dose concentration 0.5 mg/mL dosing samples collected after infusion, >98% of protein was recovered in all cases. Therefore, adsorption of protein to the inside surfaces of the IV bag, tubing and filters poses low risk. In the case of the high dose concentration, the protein recovery in all 4 component sets exceeded 99%, confirming that adsorption-driven losses are not a concern in the low and high dose concentration scenarios. The data from all component sets tested show no unusual trends.

TABLE 14

Simulated 30- and 60-Minute Infusion Time and 24 Hour IV Bag Hold Time Compatibility Study Results: Protein Concentration, Recovery and pH

| Code and Infusion Time | Ambient Temperature Hold and IV Infusion Time, t (hours, h) | [Protein] (mg/mL) Low dose conc. | [Protein] (mg/mL) High dose conc. | % Recovery Low dose conc. | % Recovery High dose conc. | pH Low dose conc. | pH High dose conc. |
|---|---|---|---|---|---|---|---|
| Set A; 30 min | Hold t = 0 | 0.54 | 7.97 | 99.5 | 99.5 | 6.0 | 6.2 |
| | Hold t = 8 | 0.55 | 7.99 | | | 6.1 | 6.2 |

TABLE 14-continued

Simulated 30- and 60-Minute Infusion Time and 24 Hour IV Bag Hold Time
Compatibility Study Results: Protein Concentration, Recovery and pH

| Code and Infusion Time | Ambient Temperature Hold and IV Infusion Time, t (hours, h) | [Protein] (mg/mL) Low dose conc. | [Protein] (mg/mL) High dose conc. | % Recovery Low dose conc. | % Recovery High dose conc. | pH Low dose conc. | pH High dose conc. |
|---|---|---|---|---|---|---|---|
| (0.5 hour infusion time) | Hold t = 24 | 0.54 | 8.01 | | | 6.0 | 6.2 |
| | Infusion t = 0.5 | 0.54 | 7.98 | | | 6.0 | 6.2 |
| Set A; 60 min (1.0 hour infusion time) | Hold t = 0 | 0.56 | 7.46 | 99.3 | 99.2 | 5.8 | 6.1 |
| | Hold t = 8 | 0.55 | 7.54 | | | NT | NT |
| | Hold t = 24 | 0.56 | 7.56 | | | NT | NT |
| | Infusion t = 1 | 0.56 | 7.40 | | | 5.8 | 6.1 |
| Set B; 30 min (0.5 hour infusion time) | Hold t = 0 | 0.55 | 7.87 | 100.1 | 100.4 | 6.0 | 6.2 |
| | Hold t = 8 | 0.55 | 7.91 | | | 6.0 | 6.2 |
| | Hold t = 24 | 0.55 | 7.83 | | | 6.0 | 6.1 |
| | Infusion t = 0.5 | 0.55 | 7.90 | | | 6.0 | 6.1 |
| Set B; 60 min (1.0 hour infusion time) | Hold t = 0 | 0.56 | 7.30 | 101.7 | 100.4 | 5.9 | 6.0 |
| | Hold t = 8 | 0.56 | 7.33 | | | NT | NT |
| | Hold t = 24 | 0.54 | 7.33 | | | NT | NT |
| | Infusion t = 1 | 0.57 | 7.32 | | | 5.9 | 6.1 |
| Set C; 60 min (1.0 hour infusion time) | Hold t = 0 | 0.57 | 7.47 | 98.1 | 100.4 | 5.8 | 6.1 |
| | Hold t = 8 | 0.57 | 7.39 | | | NT | NT |
| | Hold t = 24 | 0.56 | 7.41 | | | NT | NT |
| | Infusion t = 1 | 0.56 | 7.50 | | | 5.9 | 6.1 |
| Set D; 60 min (1.0 hour infusion time) | Hold t = 0 | 0.51 | 7.48 | 98.0 | 99.3 | 6.3 | 6.1 |
| | Hold t = 8 | 0.53 | 7.42 | | | NT | NT |
| | Hold t = 24 | 0.52 | 7.78 | | | NT | NT |
| | Infusion t = 1 | 0.50 | 7.43 | | | 6.3 | 6.2 |

NT: Not tested

2.2.3. Subvisible Particles

The subvisible particle counts by light obscuration in Table 15 also show that the 0.2 μm in-line filter effectively reduced the counts after in-line filtration during simulated 30 and 60-minute infusions. These subvisible particle counts pass USP<788> criteria for large volume injections with container size ≥100 mL.

TABLE 15

Simulated 30- and 60-Minute Infusion Time and 24 Hour Hold Time
Compatibility Study: Subvisible Particles Data

| Code | Ambient Temperature Hold Time and IV Infusion Time, t (hour, h) | ≥2 μm Count/mL Low dose conc. | ≥2 μm Count/mL High dose conc. | ≥10 μm Count/mL Low dose conc. |
|---|---|---|---|---|
| Set A; t = 30 min (0.5 hour) infusion time | Hold t = 0 | 281 | 877 | 5 |
| | Hold t = 8 | 877 | 538 | 37 |
| | Hold t = 24 | 383 | 1531 | 58 |
| | Infusion t = 0.5 | 16 | 58 | 0 |
| Set A; t = 60 min (1.0 hour) infusion time | Hold t = 0 | 1126 | 1651 | 59 |
| | Hold t = 8 | 577 | 3809 | 27 |
| | Hold t = 24 | 618 | 3045 | 32 |
| | Infusion t = 1 | 259 | 258 | 15 |
| Set B; t = 30 min (0.5 hour) infusion time | Hold t = 0 | 877 | 657 | 15 |
| | Hold t = 8 | 890 | 1301 | 25 |
| | Hold t = 24 | 385 | 415 | 8 |
| | Infusion t = 0.5 | 133 | 92 | 4 |
| Set B; t = 60 min (1.0 hour) infusion time | Hold t = 0 | 1869 | 6703 | 76 |
| | Hold t = 8 | 2035 | 3883 | 121 |
| | Hold t = 24 | 1887 | 1086 | 127 |
| | Infusion t = 1 | 167 | 247 | 23 |
| Set C; t = 60 min (1.0 hour) infusion time | Hold t = 0 | 857 | 3767 | 99 |
| | Hold t = 8 | 435 | 2873 | 19 |
| | Hold t = 24 | 935 | 895 | 135 |
| | Infusion t = 1 | 119 | 321 | 9 |

TABLE 15-continued

Simulated 30- and 60-Minute Infusion Time and 24 Hour Hold Time
Compatibility Study: Subvisible Particles Data

| Set D; t = 60 min (1.0 hour) infusion time | Hold t = 0 | 1173 | 2929 | 59 |
|---|---|---|---|---|
| | Hold t = 8 | 582 | 756 | 18 |
| | Hold t = 24 | 741 | 1409 | 19 |
| | Infusion t = 1 | 409 | 362 | 19 |

| Code | Ambient Temperature Hold Time and IV Infusion Time, t (hour, h) | ≥10 µm Count/mL Low dose conc. | ≥25 µm Count/mL High dose conc. | ≥25 µm Count/mL Low dose conc. |
|---|---|---|---|---|
| Set A; t = 30 min (0.5 hour) infusion time | Hold t = 0 | 32 | 0 | 0 |
| | Hold t = 8 | 16 | 2 | 0 |
| | Hold t = 24 | 151 | 6 | 7 |
| | Infusion t = 0.5 | 5 | 0 | 0 |
| Set A; t = 60 min (1.0 hour) infusion time | Hold t = 0 | 56 | 4 | 1 |
| | Hold t = 8 | 169 | 0 | 1 |
| | Hold t = 24 | 152 | 4 | 0 |
| | Infusion t = 1 | 9 | 1 | 0 |
| Set B; t = 30 min (0.5 hour) infusion time | Hold t = 0 | 12 | 1 | 0 |
| | Hold t = 8 | 32 | 1 | 2 |
| | Hold t = 24 | 10 | 1 | 1 |
| | Infusion t = 0.5 | 5 | 0 | 1 |
| Set B; t = 60 min (1.0 hour) infusion time | Hold t = 0 | 231 | 3 | 3 |
| | Hold t = 8 | 189 | 1 | 2 |
| | Hold t = 24 | 17 | 10 | 0 |
| | Infusion t = 1 | 3 | 2 | 0 |
| Set C; t = 60 min (1.0 hour) infusion time | Hold t = 0 | 149 | 14 | 1 |
| | Hold t = 8 | 67 | 1 | 1 |
| | Hold t = 24 | 19 | 10 | 1 |
| | Infusion t = 1 | 11 | 1 | 0 |
| Set D; t = 60 min (1.0 hour) infusion time | Hold t = 0 | 138 | 2 | 2 |
| | Hold t = 8 | 26 | 1 | 3 |
| | Hold t = 24 | 85 | 1 | 5 |
| | Infusion t = 1 | 22 | 1 | 1 |

2.2.4. Compatibility Study Results: Monomer Stability and Charge Heterogeneity Margetuximab retains its monomer stability and purity percentage in the component sets for the low dose concentration and high dose concentration solutions, as shown in Table 16 for the simulated infusion studies. Charge variant changes were minimal as detected by IE-HPLC in low and high dose concentrations.

TABLE 16

Simulated 30- and 60-Minute Infusion Time and 24 Hour Hold Time
Compatibility Study: Monomer Purity and Acidic/Basic Charge Variant Data

| Code and Infusion Time | Ambient Temperature Hold Time and IV Infusion Time, t (hours, h) | SE-HPLC Monomer Purity (%) Low dose conc. | SE-HPLC Monomer Purity (%) High dose conc. | IE-HPLC Main Peak (%) Low dose conc. | IE-HPLC Main Peak (%) High dose conc. |
|---|---|---|---|---|---|
| Set A; t = 30 min (0.5 hour) infusion time | Hold t = 0 | 99.2 | 98.9 | 41.5 | 41.1 |
| | Hold t = 8 | 99.2 | 99.0 | NT | NT |
| | Hold t = 24 | 99.1 | 99.0 | NT | NT |
| | Infusion t = 0.5 | 99.2 | 99.0 | 41.3 | 40.7 |
| Set A; t = 60 min (1.0 hour) infusion time | Hold t = 0 | 99.1 | 99.0 | 45.5 | 44.3 |
| | Hold t = 8 | 99.1 | 99.0 | NT | NT |
| | Hold t = 24 | 99.1 | 99.0 | NT | NT |
| | Infusion t = 1 | 99.2 | 99.0 | 45.9 | 44.3 |
| Set B; t = 30 min (0.5 hour) infusion time | Hold t = 0 | 99.1 | 99.0 | 41.4 | 41.4 |
| | Hold t = 8 | 99.1 | 99.0 | NT | NT |
| | Hold t = 24 | 99.1 | 99.0 | NT | NT |
| | Infusion t = 0.5 | 99.2 | 99.0 | 41.3 | 41.0 |
| Set B; t = 60 min (1.0 hour) infusion time | Hold t = 0 | 99.1 | 99.0 | 44.6 | 44.0 |
| | Hold t = 8 | 99.1 | 99.0 | NT | NT |
| | Hold t = 24 | 99.1 | 99.0 | NT | NT |
| | Infusion t = 1 | 99.1 | 99.0 | 44.1 | 44.2 |
| Set C; t = 60 min (1.0 hour) infusion time | Hold t = 0 | 99.2 | 99.0 | 45.4 | 44.6 |
| | Hold t = 8 | 99.1 | 99.0 | NT | NT |
| | Hold t = 24 | 99.1 | 99.0 | NT | NT |
| | Infusion t = 1 | 99.2 | 99.0 | 45.5 | 44.3 |
| Set D; t = 60 min (1.0 hour) infusion time | Hold t = 0 | 99.2 | 99.0 | 44.6 | 44.0 |
| | Hold t = 8 | 99.2 | 99.0 | NT | NT |
| | Hold t = 24 | 99.2 | 99.0 | NT | NT |
| | Infusion t = 1 | 99.1 | 99.0 | 44.7 | 44.1 |

NT = Not tested

2.2.5. Potency

The bioassay results demonstrated that margetuximab retains its potency during the 60-minute infusion period in both low and high dose concentration solutions in the component sets tested. Relative potency data were generated from the cell growth inhibition bioassay, and the simulated 60-minute infusion data are presented in Table 17. Data from both low and high dose concentration solutions for all 4 component sets after infusion time of 60 minutes lie within the 78-100% relative potency range. The % protein recovery for samples infused through IV lines over 30 minutes is comparable to infusion over 60 minutes and 120 minutes. Therefore, potency of margetuximab after a 30-minute infusion is expected to be representative of potency after a 60-minute infusion, since it has been shown that the protein concentration did not change during a 30- or 60-minute infusion.

TABLE 17

Simulated 60-Minute Infusion Time and 24 hour Hold Time Compatibility Study: Potency Data

| Description Code | Ambient Temperature Hold up to 24 hours and IV Infusion Time, t (hours, h) | Relative Potency (%), Cell Growth Inhibition Bioassay; Low dose concentration | Relative Potency (%), Cell Growth Inhibition Bioassay; High dose concentration |
|---|---|---|---|
| Set A t = 60 min infusion time | Infusion t = 1 | 89 | 100 |
| Set B t = 60 min infusion time | Infusion t = 1 | 93 | 89 |
| Set C t = 60 min infusion time | Infusion t = 1 | 95 | 92 |
| Set D t = 60 min infusion time | Infusion t = 1 | 86 | 78 |

2.2.6. Summary

The compatibility studies described in this section confirmed that margetuximab DP composition is stable and retains its potency, monomer purity and charge variant profile over 24 hours at ambient temperature condition when diluted into 100 mL or 250 mL 0.9% sodium chloride (saline) (through stability studies 5% Dextrose IV solution was found to be incompatible with the margetuximab composition due to excessive subvisible particle counts) in Polyvinyl chloride (PVC) IV bags or IV bags made with polyolefins (polyethylene and polypropylene) and polyamide or polyolefins only or copolymer of olefins may be used. A filtered extension set is required for IV administration of margetuximab. The use of polyethylene coated PVC infusion sets with low protein binding 0.2 μm pore size polyethersulfone (PES) in-line filters is compatible with margetuximab dose solution diluted in normal saline for dose administration. The 0.2 μm pore size PES in-line filters effectively reduced the proteinaceous visible particles and subvisible particle counts during the infusion to satisfy the USP <788> acceptance criteria and to ensure patient safety. The margetuximab dose concentrations of 0.5 to 7.2 mg/mL are stable in the above-described IV bags and IV lines for storage up to 24 hours at 2-8° C. or room temperature. The compatibility studies conducted support IV infusion of 120 minutes, and 30 minutes, using 100 mL or 250 mL normal saline IV bags.

Margetuximab DP composition (manufactured with the components of the F1 formulation) can be administered as an IV infusion at 15 mg/kg either over 120 minutes every 3 weeks, or over a minimum of 30 minutes every 3 weeks.

Example 3

Extended Stability Studies

Long term stability studies of the margetuximab DP composition in stoppered, 10 cc glass vials were performed. The stability was evaluated for a margetuximab DP composition stored in the recommended condition of 2-8° C. for up to 48 months, and stored in the accelerated condition of 25° C. for up to 6 months.

3.1 Experimental Plan

A summary of the tests used and the intervals generally evaluated in the 2-8° C., and 25° C., storage conditions are presented in Tables 18A and 18B, respectively. These studies were performed on at least three (and up to eight) different lots. The majority of the studies were conducted with the vials inverted and at least one was conducted with the vials upright.

TABLE 18A

Stability Testing Time Points Stored at 2-8° C.

| Test Description | Testing Interval (Months) | | | | | | | | | | |
|---|---|---|---|---|---|---|---|---|---|---|---|
| | 0 | 1 | 3 | 6 | 9 | 12 | 18 | 24 | 30 | 33 | 36 | 48 |
| Protein Concentration by $A_{280}$ | X | X | X | X | X | X | X | X | X | X | X |
| Potency by HER2 Binding ELISA | X | X | X | X | X | X | X | X | X | X | X |
| Potency by FcγRIIIa Binding ELISA | X | X | X | X | X | X | X | X | X | X | X |
| Potency by Cell Growth Inhibition | X | X | X | X | X | X | X | X | X | X | X |
| SE-HPLC | X | X | X | X | X | X | X | X | X | X | X |
| Reduced CE-SDS | X | X | X | X | X | X | X | X | X | X | X |
| Non-Reduced CE-SDS | X | X | X | X | X | X | X | X | X | X | X |
| IE-HPLC | X | X | X | X | X | X | X | X | X | X | X |
| Appearance | X | X | X | X | X | X | X | X | X | X | X |
| pH | X | X | X | X | X | X | X | X | X | X | X |
| Osmolality | X | X | X | X | X | X | X | X | X | X | X |
| Subvisible Particulates | X | NS | NS | X | NS | X | NS | X | X | X | X |

TABLE 18B

Stability Testing at 25 ± 2° C.

| Test Description [a] | Testing Interval (Months) | | | | |
|---|---|---|---|---|---|
| | 0 | 1 | 3 | 5 | 6 |
| Protein Concentration by A$_{280}$ | X | X | X | X | X |
| Potency by HER2 Binding ELISA | X | X | X | X | X |
| Potency by FcγRIIIa Binding ELISA | X | X | X | X | X |
| Potency by Cell Growth Inhibition | X | X | X | X | X |
| SE-HPLC | X | X | X | X | X |
| Reduced CE-SDS | X | X | X | X | X |
| Non-Reduced CE-SDS | X | X | X | X | X |
| IE-HPLC | X | X | X | X | X |
| Appearance | X | X | X | X | X |
| pH | X | X | X | X | X |
| Osmolality | X | X | X | X | X |
| Subvisible Particulates | X | NS | NS | NS | X |

Abbreviations used in Tables 18A-18B:
CCI = Container Closure Integrity;
CE-SDS = Capillary Electrophoresis - Sodium Dodecyl Sulfate;
ELISA = Enzyme Linked Immunosorbent Assay;
HPLC = High Performance Liquid Chromatography;
IE-HPLC = Ion Exchange HPLC;
SE-HPLC = Size Exclusion HPLC;
NS = Not Scheduled (indicates analysis is not required for this time point).

3.2 Results

The results of all the tests for a representative lot stored for 48 months at 2-8° C., and for 6 months at 25° C., are presented in Tables 19A-19B, and Table 20 respectively. Additional details for assay potency, purity, and protein stability (monomers and acid variants) are provided below.

TABLE 19A

Stability Data, Margetuximab DP Lot A, 2-8° C.

| Test | | Time (Months) | | | | | |
|---|---|---|---|---|---|---|---|
| | | 0 | 1 | 3 | 6 | 9 | 12 |
| Protein Concentration | | 25.9 | 25.9 | 26.0 | 26.1 | 26.1 | 26.1 |
| HER2 Binding | | 104 | 108 | 106 | 98 | 93 | 99 |
| FcγRIIIa Binding | | 76 | 81 | 92 | 103 | 106 | 110 |
| Potency, CGI Bioassay | | 107 | 105 | 108 | 99 | 91 | 92 |
| SE-HPLC | % Mono | 99.5 | 99.5 | 99.4 | 99.3 | 99.2 | 99.3 |
| | % HMW | 0.4 | 0.5 | 0.5 | 0.6 | 0.7 | 0.7 |
| | % LMW | <0.2 | <0.2 | <0.2 | <0.2 | <0.2 | <0.2 |
| Reduced CE-SDS | | 98.1 | 98.5 | 98.7 | 98.9 | 98.2 | 98.0 |
| Non-Reduced CE-SDS | | 97.3 | 97.8 | 97.7 | 97.8 | 97.2 | 97.1 |
| IE-HPLC | % MP | 46.9 | 47.1 | 46.2 | 45.2 | 43.2 | 43.1 |
| | % APG | 32.4 | 31.9 | 31.6 | 31.2 | 31.1 | 30.8 |
| | % BPG | 20.6 | 20.9 | 22.2 | 23.5 | 25.6 | 26.0 |
| Appearance, Clarity | | SO | SO | SO | SO | SO | SO |
| Appearance, Color | | L | PY | PB | PB | PB | PB |
| Appearance, Particulates | | FNP, FPP | FNP, FPP | FNP, CPP | FNP, CPP | FNP, CPP | FNP, FPP |
| pH | | 6.1 | 6.1 | 5.9 | 6.1 | 6.1 | 6.1 |
| Osmolality (mOsm/kg H$_2$O) | | 304 | 311 | 295 | 324 | 300 | 298 |
| Subvisible Particulate | P ≥ 2 μm | 5152 | NS | NS | 6348 | NS | 5295 |
| | P ≥ 10 μm | 51 | NS | NS | 29 | NS | 85 |
| | P ≥ 25 μm | 1 | NS | NS | 0 | NS | 7 |

TABLE 19B

Stability Data, Margetuximab DP Lot A, 2-8° C.

| Test | | Time (Months) | | | | | |
|---|---|---|---|---|---|---|---|
| | | 18 | 24 | 30 | 33 | 36 | 48 |
| Protein Concentration | | 26.0 | 26.0 | 26.1 | 26.0 | 26.2 | 26.0 |
| HER2 Binding | | 93 | 98 | 99 | 93 | 93 | 88 |
| FcγRIIIa Binding | | 105 | 100 | 103 | 107 | 107 | 101 |
| Potency, CGI Bioassay | | 98 | 92 | 98 | 75 | 94 | 74 |
| SE-HPLC | % Mono | 99.1 | 99.2 | 99.0 | 99.1 | 99.0 | 98.9 |
| | % HMW | 0.7 | 0.6 | 0.7 | 0.7 | 0.8 | 0.8 |
| | % LMW | 0.2 | 0.2 | 0.2 | 0.2 | 0.3 | 0.3 |
| Reduced CE-SDS | | 98.3 | 98.1 | 98.4 | 98.1 | 98.2 | 98.1 |
| Non-Reduced CE-SDS | | 97.4 | 97.1 | 97.2 | 97.1 | 97.2 | 96.8 |
| IE-HPLC | % MP | 38.3 | 34.9 | 32.2 | 31.5 | 30.6 | 25.9 |
| | % APG | 33.0 | 33.7 | 35.9 | 35.5 | 36.8 | 37.3 |
| | % BPG | 28.7 | 31.4 | 32.0 | 32.9 | 32.6 | 36.8 |
| Appearance, Clarity | | SO | SO | SO | SO | SO | SO |
| Appearance, Color | | PB | L | L | L | L | L |
| Appearance, Particulates | | FNP, CPP | FNP, FPP | FNP, FPP | FNP, FPP | FNP, FPP | FNP, FPP |
| pH | | 6.1 | 6.1 | 6.1 | 6.1 | 6.1 | 6.1 |
| Osmolality (mOsm/kg H$_2$O) | | 293 | 296 | 298 | 297 | 296 | 298 |
| Subvisible Particulate | P ≥ 2 μm | NS | 5472 | 5000 | 6206 | 4825 | 6009 |
| | P ≥ 10 μm | NS | 29 | 18 | 20 | 21 | 28 |
| | P ≥ 25 μm | NS | 1 | 0 | 0 | 0 | 0 |

TABLE 20

Stability Data, Margetuximab DP Lot A, 25 ± 2° C.

| Test | | Time (Months) | | | | | | |
|---|---|---|---|---|---|---|---|---|
| | | 0 | 1 | 2 | 3 | 4 | 5 | 6 |
| Protein Concentration | | 25.9 | 25.9 | 26.0 | 26.0 | 26.1 | 25.9 | 25.9 |
| HER2 Binding | | 104 | 100 | 79 | 77 | 72 | 104 | 100 |
| FcγRIIIa Binding | | 76 | 82 | 100 | 99 | 104 | 76 | 82 |
| Potency, CGI Bioassay | | 107 | 91 | 75 | 58 | 49 | 107 | 91 |
| SE-HPLC | % Mono | 99.5 | 99.3 | 99.0 | 98.8 | 98.6 | 99.5 | 99.3 |
| | % HMW | 0.4 | 0.6 | 0.7 | 0.9 | 1.0 | 0.4 | 0.6 |
| | % LMW | <0.2 | <0.2 | 0.2 | 0.4 | 0.4 | <0.2 | <0.2 |
| Reduced CE-SDS | | 98.1 | 98.4 | 98.4 | 97.7 | 98.3 | 98.1 | 98.4 |
| Non-Reduced CE-SDS | | 97.3 | 97.6 | 96.9 | 96.1 | 95.9 | 97.3 | 97.6 |
| IE-HPLC | % MP | 46.9 | 42.3 | 29.1 | 21.6 | 18.6 | 46.9 | 42.3 |
| | % APG | 32.4 | 32.2 | 40.5 | 48.3 | 52.0 | 32.4 | 32.2 |
| | % BPG | 20.6 | 25.5 | 30.5 | 30.1 | 29.4 | 20.6 | 25.5 |
| Appearance, Clarity | | SO | SO | SO | SO | SO | SO | SO |
| Appearance, Color | | L | L | PB | PY | PB | L | L |
| Appearance, Particulates | | FNP, FPP | FNP, CPP | FNP, CPP | FNP, CPP | FNP, CPP | FNP, FPP | FNP, CPP |
| pH | | 6.1 | 6.2 | 6.2 | 6.1 | 6.2 | 6.1 | 6.2 |
| Osmolality (mOsm/kg H$_2$O) | | 304 | 307 | 299 | 300 | 324 | 304 | 307 |
| Subvisible Particulate | P ≥ 2 μm | 5152 | NS | NS | NS | 4157 | 5152 | NS |
| | P ≥ 10 μm | 51 | NS | NS | NS | 51 | 51 | NS |
| | P ≥ 25 μm | 1 | NS | NS | NS | 1 | 1 | NS |

Abbreviations used in Tables 19A-19B and Table 20:
CGI = Cell Growth Inhibition;
SE-HPLC: % HMW = % High Molecular Weight species, % LMW = % Low Molecular Weight species;
MP = main peak, APG = acidic peak group, BPG = basic peak group;
C = clear;
SO = slightly opalescent;
L = colorless;
PY = pale yellow;
PB = pale brown;
FNP = essentially free from visible foreign particles;
MPP = may contain visible proteinaceous particles;
FPP = essentially free from visible proteinaceous particles;
CPP = contains visible proteinaceous particles;
NS = Not scheduled; indicates test is not required for this time point.

3.2.1. Potency Assay Stability Data

For the FcR binding ELISA, there was no, or only a minimal, trend in the potency data at either the recommended or the accelerated storage temperature. Both the HER2 binding ELISA and the cell growth inhibition (CGI) bioassay showed some minor decrease in relative potency over time at the recommended storage temperature of 2-8° C. The CGI bioassay is the more sensitive potency assay between the CGI bioassay and the HER2 binding ELISA in terms of stability-indication; the average slope of the HER2 binding ELISA at the recommended storage temperature was −0.17%/month while the average slope of the CGI Bioassay was −0.45%/month.

Similar trends were evident at the accelerated storage temperature of 25° C. The average slope of the HER2 binding ELISA at the accelerated storage temperature was −4.7%/month while the average slope of the CGI bioassay was −7.8%/month.

3.2.2. SE-HPLC Stability Data Summary

SE-HPLC was used to monitor the % Monomer, % HMW and % LMW. There was no, or minimal, change in % LMW at the recommended storage temperature of 2-8° C. There was a minor trend in the % Monomer and % HMW data at the recommended storage temperature; % Monomer deceases and % HMW increases, each at a rate of approximately 0.01%/month, well within acceptable levels over the 48 months of monitoring.

At the accelerated stability temperature, the rate of % HMW increase was approximately 0.08%/month, which was faster than at the recommended storage temperature, but still kept the % HMW at acceptable levels through 6 months of monitoring. The % Monomer dropped at a faster rate at the accelerated temperature than in the recommended storage temperature, and stayed within acceptable levels through 6 months of monitoring.

3.2.3. CE-SDS Stability Data Summary

Purity was monitored over time by capillary electrophoresis, specifically Reduced CE-SDS and Non-reduced CE-SDS. There was minimal trend in the % Purity results for both Reduced CE-SDS and Non-reduced CE-SDS at the recommended storage temperature of 2-8° C. The pooled slopes were −0.01%/month for Reduced CE-SDS and −0.02%/month for Non-reduced CE-SDS, indicating that the purity was maintained within acceptable levels over the 48 months of monitoring. At the accelerated storage condition of 25° C. these rates increased to −0.24%/month for Reduced CE-SDS and −0.43%/month for Non-reduced CE-SDS, but stayed within acceptable levels through 6 months of monitoring.

3.2.4. IE-HPLC Stability Data Summary

Charge variants (% Acidic Peak Group (% APG), and % Basic Peak Group (% BPG)) and the main peak of margetuximab (% Main Peak) were monitored over time by IE-HPLC data. At the recommended storage temperature, % Main Peak decreased at a rate of −0.46%/month, while % APG increased at a rate of 0.16%/month and % BPG increased at a rate of 0.30%/month. The difference in relative rates of change between the accelerated and recommended storage condition trends is due to different temperature-dependence of individual degradation reactions which contribute to the acidic and basic variant peaks.

3.3. Stability Conclusions

The above analyses of quantitative data from stability-indicating methods for multiple lots supports a shelf-life of at least 36 months at the recommended storage condition of 2-8° C. The representative stability data shown in Tables 19A-19B and Table 20 indicates that all other tests, qualitative and semi- or non-quantitative, also remained within acceptable limits through at least 36 months and support a shelf-life at least about 36 months.

Example 4

Materials and Methods 4.1 Subvisible Particulates By HIAC Liquid Particle Counting Particle count analysis was carried out according to USP <787>"Light Obscuration Particle Count Test". An electronic liquid-borne particle-counting system using a light obscuration sensor is employed (HIAC). Particles are counted in three size ranges: ≥2 μm, ≥10 μm, and ≥25 μm. Analysis was performed on samples stored at 2-8° C. and 25° C.

4.2 Appearance

Appearance is assessed visually under good visible light meeting minimum intensity requirements, in front of both a white and a black background. Sample aliquots are assessed in clear glass vials. Attributes examined include color of solution and clarity of solution. The appearance procedure is aligned with USP<790> and Ph.Eur. 2.2.2.

4.3 Monomeric Purity by Size Exclusion High Performance Liquid Chromatography (SE-HPLC)

SE-HPLC was used essentially as described here to measure product purity. Samples are diluted to a final concentration of 1 mg/mL in phosphate-buffered saline. Samples are injected (50 μg per injection) onto an SE-HPLC column (TSK-Gel G3000SW$_{XL}$, 7.8 mm×30 cm, 5 μm particles, pore size 250 Å) at a flow rate of 0.5 mL/min, and are eluted isocratically with sodium phosphate/sodium sulfate buffer. The run time is 30 minutes. Eluted proteins are detected using ultraviolet (UV) absorbance at 280 nm. The reportable result is the monomer purity, calculated as the area percent of the product monomer peak (compared to all peaks excluding the peaks of excipients). Also reported is the total percent of all non-excipient species with apparent molecular weight greater than the IgG monomer (called High Molecular Weight Species, or HMW), and the total percent of all non-excipient species with apparent molecular weight lower than the IgG monomer (called Low Molecular Weight Species, or LMW). HMW are consistent with dimers, trimers, and larger oligomers of IgG. LMW may consist of partial molecules, antibody fragments, and free light and heavy chains.

4.4 Charge Heterogeneity and Identity by Ion Exchange Chromatography (IE-HPLC)

IE-HPLC was used for charge heterogeneity testing essentially as described here. Samples are diluted to a final concentration of 2.5 mg/mL in Mobile Phase A [20 mM 2-(N-morpholino) ethanesulfonic acid (IVIES), pH 6.5]. Samples are injected (100 μg per injection) onto an ion exchange HPLC column (Thermo Scientific ProPac WCX-10 analytical column, 4×250 mm, 5 μm particles) at a flow rate of 0.5 mL/min and a constant column temperature of 35° C. A linear elution gradient is applied from 5% to 25% Mobile Phase B (20 mM IVIES, 0.5 M NaCl, pH 6.5), followed by column regeneration using first 100% and then 5% Mobile Phase B. The total run time is 75 minutes. Eluted proteins are detected using ultraviolet (UV) absorbance at 280 nm. The various charged product species are resolved into populations of main peak, acidic peak group (APG), and basic peak group (BPG), which are reported for charge heterogeneity as percent of the total peak area (i.e., % Main Peak, % APG, and % BPG).

4.5 Charge Heterogeneity and Identity by cIEF

Alternatively, the charge heterogeneity and identity of margetuximab can be evaluated by capillary isoelectric focusing (cIEF). For example, cIEF can be performed using an iCE3 System with an Alcott 720NV Autosampler (ProteinSimple). For such analysis, an margetuximab Reference Standard and test article samples are prepared containing carrier ampholytes and pI markers, and are loaded into a capillary cartridge for analysis. The electrolytic tanks at each end of the capillary are filled with anolyte and catholyte solutions. Voltage is applied and the samples are focused at their pI. A camera takes a UV light absorption image of the entire capillary column at frequent regular intervals (e.g., every 30 seconds), allowing real time monitoring of the focusing step. The resulting separation pattern image is captured and analyzed with chromatography data system software. The test article electrophoretic profile is compared to the Reference Standard electrophoretic profile. The reportable results of the assay are the average main charge peak % area, the average acidic variants % area, and the average basic variants % area, of duplicate preparations.

To confirm identity, if required, the pI of the main peak of the test article should be within 0.5 pI units of the pI of the main peak of the margetuximab Reference Standard, and the test article profile must compare qualitatively to that of the Reference Standard, within a given sample set.

4.6 Purity by Reduced CE-SDS

The reduced sodium dodecyl sulfate capillary electrophoresis method (reduced CE-SDS) provides quantitative information on product purity, by providing separation of the denatured, disassociated and reduced light chain (LC) and heavy chain (HC) from product-related substances and impurities such as light and heavy chain fragments and non-reducible adducts. Margetuximab test articles are diluted first to 2 mg/mL in water, and then diluted 2-fold further into 2x sample buffer containing SDS and a reducing agent, β-mercaptoethanol. Samples are heated to 70° C. for 10 minutes to reduce and denature the protein, and then cooled to room temperature. Samples are injected electro-kinetically into a SDS gel-filled bare-fused silica capillary (50 μm internal diameter) to which an electric field is applied using a Sciex Capillary Electrophoresis System (formerly Beckman Coulter and AB Sciex), and protein components are separated based on differences in their hydrodynamic size. Separated protein components are detected by UV absorbance at 220 nm. The reportable result is the % product purity, calculated as the sum of the % HC and % LC, using the velocity-corrected peak area percents.

4.7 Purity by Non-Reduced CE-SDS

The non-reduced sodium dodecyl sulfate capillary electrophoresis method (non-reduced CE-SDS) provides quantitative information on intact monomer purity, by providing separation of the denatured but intact IgG from product-related substances and impurities such as antibody fragments, unassociated heavy or light chains, and covalent antibody oligomers. Margetuximab test articles are diluted first to 2 mg/mL in water, and then diluted 2-fold further into 2x sample buffer containing SDS and an alkylating agent, iodoacetamide. Samples are heated to 70° C. for 10 minutes to denature the protein, and then cooled to room temperature. Samples are injected electro-kinetically into a SDS gel-filled bare-fused silica capillary (50 μm internal diameter) to which an electric field is applied using a Sciex Capillary Electrophoresis System (formerly Beckman Coulter and AB Sciex), and protein components are separated based on differences in their hydrodynamic size. Separated protein components are detected by UV absorbance at 220 nm. The reportable result is the % main peak (i.e., intact IgG), calculated using the velocity-corrected peak area percents.

4.8 Potency by HER2 Binding ELISA

An indirect enzyme-linked immunosorbent assay (ELISA) that quantitates binding activity of margetuximab to HER2 protein was performed essentially as described here. Soluble HER2 fusion protein, rhErbB2/Fc (HER2/ErbB2/neu Fc chimera), is coated to the solid phase (96-well assay plates). Serially-diluted margetuximab sample is allowed to bind to the coated rhErbB2/Fc. A dilution series of both the Test Article and of a margetuximab Reference Standard (RS) are tested in this manner, to generate dose-response curves. An alkaline phosphatase (AP)-conjugated goat anti-human kappa antibody is then added and allowed to bind to the complex of margetuximab and rhErbB2/Fc. Quantitation of bound conjugated antibody is achieved by addition of a colorimetric AP substrate. Oxidation of the added AP substrate by the conjugated AP yields a color product that can be measured at 405±10 nm. The absorbance response detected is proportional to the amount of margetuximab present. Data are fitted to a constrained four-parameter logistic model to describe absorbance as a function of margetuximab concentration. The reportable result, the potency of the test article relative to the Margetuximab Reference Standard, is calculated using the following formula:

$$\text{Relative Potency} = EC_{50} \text{ Reference Standard}/EC_{50} \text{ Test Article.}$$

4.9 Potency by FcγRIIIa Binding ELISA

Margetuximab contains point mutations in the Fc-domain that enhance the interaction of the margetuximab constant region with some human Fc receptors, in particular the Fcγ Receptor subtype IIIa (FcγRIIIa), also referred to as CD16a. The potency of the Fc domain is assessed with an indirect competitive enzyme linked immunosorbent assay (ELISA) essentially as described. The quantification of the binding of margetuximab test article Fc to the FcγRIIIa is measured by its ability to compete against the binding of a biotin-labeled margetuximab competitor sample (MGAH22-Bt). To perform the assay, soluble recombinant human FcγRIIIa is coated to the solid phase (96-well assay plates). A dilution series of margetuximab Test Article (TA) in a constant concentration of MGAH22-Bt is allowed to bind to the immobilized FcγRIIIa. A dilution-series of the test article and of the margetuximab Reference Standard is analyzed in this manner on the same assay plate, in order to generate dose-response curves for both the test article and the margetuximab Reference Standard. Detection of bound MGAH22-Bt is achieved by addition of Alkaline Phosphatase conjugated with Streptavidin (Streptavidin-AP), followed by a colorimetric AP substrate. Oxidation of the added AP substrate by the conjugated AP yields a color product that can be measured at 405±10 nm. The intensity (absorbance) of the color signal is measured using a microplate reader. The level of color signal is proportional to the amount of bound MGAH22-Bt. Data are fitted to a constrained four-parameter logistic model to describe absorbance signal as a function of margetuximab concentration. The reportable result, the potency of the test article relative to the margetuximab Reference Standard, is calculated using the following formula:

$$\text{Relative Potency} = 100\% \times IC_{50} \text{ Reference Standard}/IC_{50} \text{ Test Article}$$

4.10 Potency Assay Cell Growth Inhibition (CGI) Assay

The CGI assay was performed essentially as described here. BT-474 cells are plated in each well of a 96-well plate and allowed to settle and adhere to the wells overnight at 37° C. The next day, serially diluted margetuximab Reference Standard and Test Article are added to the assay plate. These dilutions of antibody are incubated with the cells in culture media for 6 days at 37° C. The potency of margetuximab is determined by monitoring the proliferation of BT-474 cells, using CellTiter-Glo® Luminescent Cell Viability Assay Kit (Promega), which quantifies the amount of ATP present in the assay plate wells by producing a luminescent signal. The amount of luminescence is directly proportional to the number of viable cells in each well. The dose response curves are fitted to a constrained four-parameter logistic model. The reportable result, the potency of the test article relative to the margetuximab Reference Standard, is calculated using the following formula:

$$\text{Relative Potency} = 100\% \times IC_{50}\text{ Reference Standard}/IC_{50}\text{ Test Article}.$$

All publications and patents mentioned in this specification are herein incorporated by reference to the same extent as if each individual publication or patent application was specifically and individually indicated to be incorporated by reference in its entirety.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth. Such modifications and variations are intended to fall within the scope of the disclosure and/or the appended claims. It is to be understood that this disclosure is not limited to particular methods, compounds, or compositions, which may of course vary. It is also to be understood that the terminology used herein is for the purpose of describing particular embodiments only, and is not intended to be limiting.

What is claimed is:

1. A pharmaceutical composition comprising:
   (a) margetuximab at a concentration of from about 20 mg/mL to about 100 mg/mL;
   (b) sodium chloride at a concentration of from about 2.47 mg/mL to about 3.34 mg/mL;
   (c) L-arginine hydrochloride at a concentration of from about 9.35 mg/mL to about 12.75 mg/mL;
   (d) sucrose at a concentration of from about 25.5 mg/mL to about 34.5 mg/mL;
   (e) polysorbate 80 ("PS80") at a concentration of from about 0.05 mg/mL to about 0.20 mg/mL;
   (f) a sodium phosphate buffer of:
      (1) sodium phosphate monohydrate at a concentration of from about 0.94 mg/mL to about 1.27 mg/mL; and
      (2) sodium phosphate dibasic heptahydrate at a concentration of from about 0.49 mg/mL to about 0.67 mg/mL; and
   (g) water;
   wherein said composition has a pH of from about 5.8 to about 6.4.

2. The pharmaceutical composition of claim 1, wherein said concentration of said margetuximab is from about 21.25 mg/mL to about 28.75 mg/mL.

3. A pharmaceutical composition comprising:
   (a) margetuximab at a concentration of from about 22.5 mg/mL to about 27.5 mg/mL;
   (b) sodium chloride at a concentration of about 2.9 mg/mL;
   (c) L-arginine hydrochloride at a concentration of about 11 mg/mL;
   (d) sucrose at a concentration of about 30 mg/mL;
   (e) polysorbate 80 ("PS80") at a concentration of about 0.1 mg/mL;
   (f) a sodium phosphate buffer of:
      (1) sodium phosphate monohydrate at a concentration of from about 1.08 mg/mL to about 1.1 mg/mL; and
      (2) sodium phosphate dibasic heptahydrate at a concentration of about 0.58 mg/mL; and
   (g) water;
   wherein said composition has a pH of from about 5.8 to about 6.4.

4. The pharmaceutical composition of claim 3, wherein said pharmaceutical composition comprises said margetuximab at a concentration of about 25 mg/mL.

5. The pharmaceutical composition of claim 1, wherein said composition has a shelf-life of at least about 18 months at 2-8° C.

6. The pharmaceutical composition of claim 1, wherein said composition has an osmolality of from about 270 mOsm/kg $H_2O$ to about 330 mOsm/kg $H_2O$.

7. The pharmaceutical composition of claim 1, wherein said composition maintains the charge heterogeneity profile of said margetuximab for at least about 18 months at about 2-8° C.

8. A container comprising the pharmaceutical composition of claim 1, wherein said container comprises about 10 mL volume of said pharmaceutical composition.

9. A container comprising the pharmaceutical composition of claim 2, wherein said container comprises about 10 mL volume of said pharmaceutical composition.

10. A container comprising the pharmaceutical composition of claim 3, wherein said container comprises about 10 mL volume of said pharmaceutical composition.

11. A sealed package comprising the container of claim 8.

12. A sealed package comprising the container of claim 9.

13. A sealed package comprising the container of claim 10.

* * * * *

SEQUENCE LISTING

```
<160> NUMBER OF SEQ ID NOS: 2

<210> SEQ ID NO 1
<211> LENGTH: 450
<212> TYPE: PRT
<213> ORGANISM: Artificial Sequence
<220> FEATURE:
<223> OTHER INFORMATION: Amino Acid Sequence of the Heavy Chain of
      Margetuximab

<400> SEQUENCE: 1

Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Val Gly Gly
225                 230                 235                 240

Pro Ser Val Phe Leu Leu Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Leu Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Leu Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Amino Acid Sequence of the Light Chain of
      Margetuximab

<400> SEQUENCE: 2

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210
```